US011635379B2

(12) United States Patent
Palanisami et al.

(10) Patent No.: US 11,635,379 B2
(45) Date of Patent: Apr. 25, 2023

(54) PORTABLE WIDE FIELD FLUORIMETER SYSTEMS

(71) Applicant: The General Hospital Corporation, Boston, MA (US)

(72) Inventors: Akilan Palanisami, Cambridge, MA (US); Tayyaba Hasan, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 160 days.

(21) Appl. No.: 16/479,152

(22) PCT Filed: Jan. 19, 2018

(86) PCT No.: PCT/US2018/014563
§ 371 (c)(1),
(2) Date: Jul. 18, 2019

(87) PCT Pub. No.: WO2018/136819
PCT Pub. Date: Jul. 26, 2018

(65) Prior Publication Data
US 2020/0041413 A1 Feb. 6, 2020

Related U.S. Application Data

(60) Provisional application No. 62/448,455, filed on Jan. 20, 2017.

(51) Int. Cl.
*B01L 3/00* (2006.01)
*B01L 7/00* (2006.01)
(Continued)

(52) U.S. Cl.
CPC ........ *G01N 21/645* (2013.01); *B01L 3/50273* (2013.01); *B01L 3/502715* (2013.01);
(Continued)

(58) Field of Classification Search
CPC ................. G01N 21/645; G01N 21/76; G01N 2021/6471; G01N 2333/195;
(Continued)

(56) References Cited

U.S. PATENT DOCUMENTS 6,914,677 B2 7/2005 Mader et al.
6,915,679 B2 7/2005 Chien et al.
(Continued)

FOREIGN PATENT DOCUMENTS

WO WO 2016/061453 4/2016

OTHER PUBLICATIONS

International Search Report and Written opinion dated Jun. 1, 2018 in international application No. PCT/US2018/014563, 22 pgs.
(Continued)

*Primary Examiner* — Christine T Mui
(74) *Attorney, Agent, or Firm* — Fish & Richardson P.C.

(57) ABSTRACT

The present disclosure features portable wide field fluorimeter systems, e.g., in the form of low-cost mobile platforms, and methods to perform fluorometric assays to detect a change in fluorescence intensity in liquid samples, e.g., caused by the presence of a target analyte, e.g., a protein, e.g., an enzyme (e.g., β-lactamase) expressed by a target pathogen in a liquid sample in a point-of-care setting. In some implementations, a portable system for detecting a change in fluorescence intensity in a liquid sample includes a microfluidic device, an optical assembly including an emission filter and one or more lenses, and an analyzer device that collects and processes a fluorescent signal for the detection of a target analyte produced by the target pathogen present in the liquid sample.

19 Claims, 25 Drawing Sheets

(51) Int. Cl.
  *G01N 21/64* (2006.01)
  *G01N 21/76* (2006.01)
  *C12Q 1/04* (2006.01)

(52) U.S. Cl.
  CPC ... *B01L 3/502753* (2013.01); *B01L 3/502761* (2013.01); *B01L 7/00* (2013.01); *C12Q 1/04* (2013.01); *C12Y 305/02006* (2013.01); *G01N 21/76* (2013.01); *B01L 2300/023* (2013.01); *B01L 2300/042* (2013.01); *B01L 2300/06* (2013.01); *B01L 2300/0609* (2013.01); *B01L 2300/0654* (2013.01); *B01L 2300/12* (2013.01); *B01L 2300/168* (2013.01); *B01L 2300/1805* (2013.01); *B01L 2400/0487* (2013.01); *G01N 2021/6471* (2013.01); *G01N 2333/195* (2013.01); *G01N 2333/986* (2013.01)

(58) Field of Classification Search
  CPC ......... G01N 2333/986; B01L 3/502715; B01L 3/5027; B01L 3/502; B01L 3/50273; B01L 3/502753; B01L 3/502761; B01L 2300/023; B01L 2300/042; B01L 2300/06; B01L 2300/0609; B01L 2300/0654; B01L 2300/12; B01L 2300/168; B01L 2300/1805; B01L 2400/0487; B01L 7/00
  USPC ...................................... 422/82.07
  See application file for complete search history.

(56) References Cited

U.S. PATENT DOCUMENTS

| | | | |
|---|---|---|---|
| 2011/0253224 A1* | 10/2011 | Linder | G01N 21/59 137/2 |
| 2015/0362512 A1* | 12/2015 | Lippert | G01N 21/76 436/110 |
| 2016/0176933 A1* | 6/2016 | Boyden | G01N 33/502 514/21.2 |

OTHER PUBLICATIONS

International Preliminary Report on Patentability dated Jul. 23, 2019 in International Application No. PCT/US2018/014563, 11 pgs.

\* cited by examiner

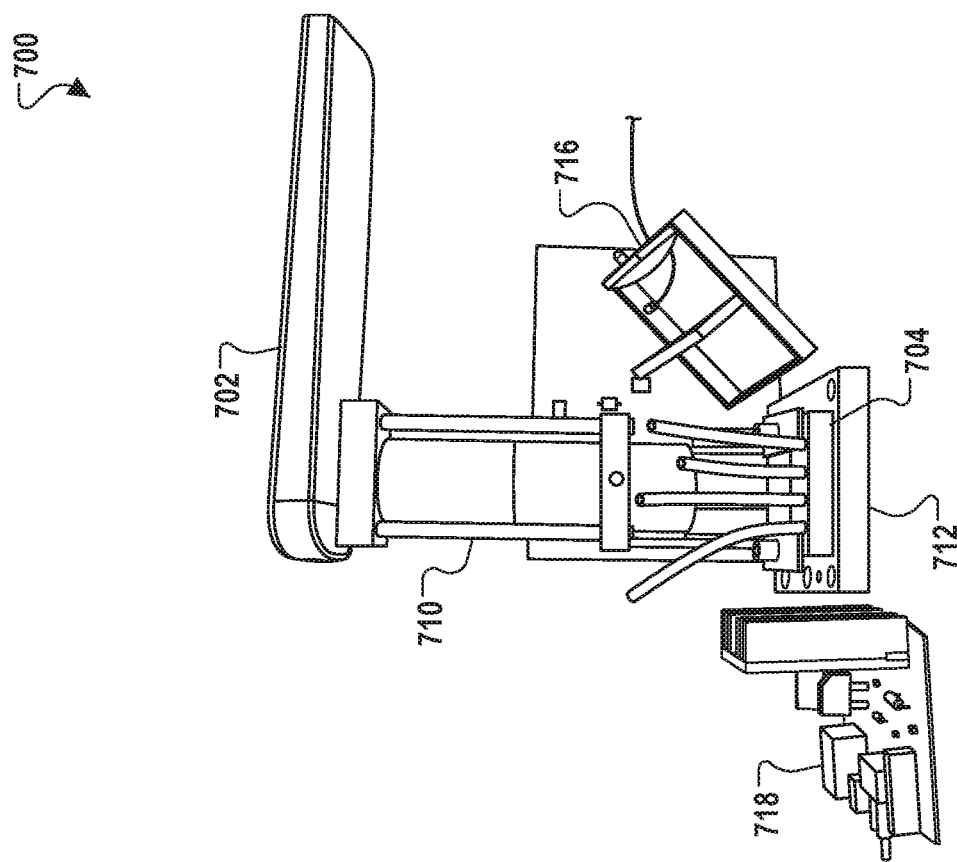
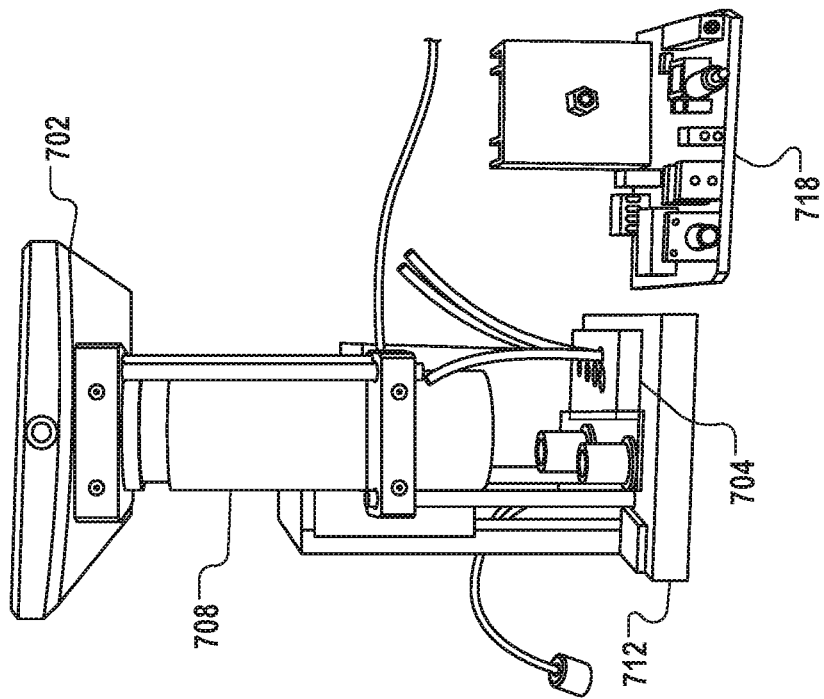
FIG. 7D
FIG. 7C

PORTABLE WIDE FIELD FLUORIMETER SYSTEMS

CROSS-REFERENCE TO RELATED APPLICATIONS

This application is a § 371 National Stage Application of PCT/US2018/014563, filed Jan. 19, 2018, which claims the benefit of U.S. Provisional Patent Application No. 62/448,455 filed on Jan. 20, 2017, which is incorporated herein by reference in its entirety.

TECHNICAL FIELD

The present application relates to systems and methods for performing fluoroscopy in a biological fluid sample.

BACKGROUND

Fever is often the most common cause for medical consultation in children, especially neonates (<3 months old). While many of these cases often self-resolve, approximately 10% of such patients develop a serious bacterial illness (SBI) such as a urinary tract infection (UTI), bacteremia, or meningitis. UTI is the most common and places the child at risk for renal scarring and consequent renal failure later in life, particularly if effective treatment is delayed. Sepsis/meningitis can also be concerning, as it is the third most common cause of death for children under the age of 5, with the first two months of childhood being the most dangerous period. Prompt diagnosis is critical in these circumstances as delayed treatment is often correlated with poor clinical outcomes for these patients. However, early diagnosis of neonatal meningitis is often difficult to establish clinically as the signs are minimal and broadly overlap with UTI. These problems are especially serious in southeast Asia, where at least 50,000 child deaths occur each year due to meningitis. Approximately forty percent of survivors develop neurological sequelae (e.g., deafness).

Treatment for SBI in infants and children is generally aggressive, with early administration of a broad-spectrum antibiotic, such as a third generation cephalosporin. However, this can be complicated by the spread of antibiotic resistance (AR). For example, there has been increasing resistance to broadly used classes of antibiotics (e.g., β-lactams, which includes cephalosporins) by many of the most common sources of SBI, such as *Escherichia coli, Klebsiella pneumoniae, Enterobacter* sp, and *Haemophilus influenzae*. Studies of neonatal SBI in Southeast Asia suggest roughly one third of these infections are resistant to third generation cephalosporins, with most of the resistance stemming from β-lactamases, which enzymatically cleave β-lactam antibiotics. In addition, there are many known β-lactamases with different resistance profiles, which complicates the administration of effective treatment. Extended spectrum β-lactamases (ESBL), which can destroy third generation cephalosporins are especially problematic, because they can be the most common reason for empiric antibiotic treatment failure in the febrile child. Carbapenem antibiotics (e.g., imipenem) are often prescribed in this case, but these can be neutralized by even more potent β-lactamases (carbapenemases) and have become a significant concern.

The standard practice for identifying AR is laboratory culture of patient specimens. However, the degree of precision required for minimum inhibitory concentration (MIC) testing of ESBL is often not available, even in high-income countries, and can be impractical in many low and middle-income countries (LMIC). Such testing is often too slow in any case to inform initial treatment (e.g., culture requires 1-3 days). Because of this, AR is not well monitored on a regional scale, clouding the extent of the problem and complicating resource allocation, since understanding the epidemiology is critical to formulating an effective health policy (which includes vaccinations, education, as well as antibiotic guidelines). Identification of ESBL/carbapenemase derived AR is important to promote effective patient treatment and regional health planning. PCR-based tests can be used as an alternative, but often requires a comprehensive set of gene sequences to identify different types of potential β-lactamase expression. Thus, cost-effective methods to characterize β-lactamase resistance at the point of care (POC) are limited or do not presently exist.

SUMMARY

The present disclosure features portable wide field fluorimeter systems, e.g., in the form of low-cost mobile platforms, and methods to perform fluorometric assays to detect a change in fluorescence intensity in liquid samples, e.g., caused by the presence of a target analyte, e.g., a protein, e.g., an enzyme (e.g., β-lactamase) expressed by a target pathogen in a liquid sample in a point-of-care setting. The systems can use a detection reagent that includes a fluorescent probe designed to detect a specific enzymatic process, e.g., to detect the presence of a specific enzyme, such as beta-lactamase, expressed by a target pathogen (e.g., an antibiotic resistant bacteria). Results of the fluorometric assay can be used to determine antibiotic susceptibility directly from patient samples over a short time period (e.g., less than 20 minutes). The systems can be designed perform a fluorometric assay in areas with limited healthcare infrastructure, such as field sites in LMICs.

The systems can include a microfluidic device that processes a patient sample and a detection reagent specific to a protein, e.g., enzyme, expressed by a target pathogen, an analyzer device with an optical assembly to collect and process a fluorescent signal associated with the fluorometric assay, and interface electronics to provide fine-tuned control over signal detection and processing. In some implementations, the portable analyzer device can be a mobile device, such as a mobile phone, a tablet computing device, a personal digital assistant, and/or a laptop computing device.

In one general aspect, the present disclosure features microfluidic devices for detecting a change in fluorescence intensity in a liquid sample. The devices include a housing. The housing includes an inlet that receives a liquid sample, an outlet for receiving the liquid sample from the inlet, a filter arranged between the inlet and the outlet and located to retain the target analyte, and a fluidic circuit arranged within the housing. The fluidic circuit includes a first channel in fluid communication with the inlet. The first channel extends from the inlet to a first surface of the filter. The fluidic circuit also includes a second channel in fluid communication with the outlet. The second channel extends from a second surface of the filter that is opposite to the first surface of the filter to the outlet. The second channel is shaped and dimensioned to collect the liquid sample that has passed through the filter and has a depth that reduces an amount of unreacted detection reagent available to create background fluorescence during detection of the target analyte.

In some implementations, the devices are constructed from multiple layers. The multiple layers can include a first layer including a first hole corresponding to the inlet and a second hole corresponding to the outlet. The multiple layers also include a second layer arranged adjacent to the first layer and including a first hole aligned with the first hole of the first layer, and a second hole aligned with the second hole of the first layer. The multiple layers include a third layer arranged adjacent to the second layer and including a portion of the first channel in communication with the first hole of the second layer, and a hole aligned with the second hole of the second layer. The multiple layers include a fourth layer arranged adjacent to the third layer and including another portion of the first channel in communication with the portion of the first channel in the third layer, a hole aligned with the hole of the third layer, and a portion that is arranged adjacent to the first surface of the filter. The multiple layers include a fifth layer arranged adjacent to the fourth layer and including a hole aligned to the portion of the first channel in the fourth layer, a portion attached to the second surface of the filter, and a hole aligned with the hole of the fourth layer. The multiple layers include a sixth layer arranged adjacent to the fifth layer and including the second channel in communication with the hole of the fifth layer. The multiple layers include a seventh layer arranged adjacent to the sixth layer and an eighth layer arranged adjacent to the seventh layer.

In some implementations, the first, third, sixth, and eight layers include an acrylic material, and the second, fourth, fifth, and seventh layers include a double-sided adhesive.

In some implementations, the device further includes a flow control device coupled to the housing and in communication with the first channel through the outlet. The flow control device is configured and controlled to supply a negative pressure to the fluidic circuit to cause a volume of liquid sample to pass through the filter towards the outlet. In certain implementations, the flow control device includes a plug member that is slidably disposed within a second outlet of the housing, and the second outlet is in fluid communication with the first and second channels. In other implementations, the flow control device is a syringe fluidly coupled to the second outlet.

In some implementations, the filter includes pores that are sized to be smaller than the target analyte. In some implementations, at least one or both of the first surface of the filter and one or more surfaces defining the first channel are partially or entirely coated with a fluorescent probe specific to an enzyme produced by the target pathogen.

In another general aspect, the present disclosure features portable systems for detecting a change in fluorescence intensity in a liquid sample. The systems include the microfluidic devices described herein. The systems also include an optical assembly including an emission filter and one or more lenses, and an analyzer device that collects and processes a fluorescent signal for the detection of a target analyte produced by the target pathogen present in the liquid sample. In some implementations, the analyzer device is a mobile phone, and the fluorescent signal is collected by a camera of the mobile phone.

In some implementations, the systems include a housing. The housing includes the optical assembly, a holder for securing the mobile phone and aligning the camera of the mobile phone with the optical assembly, the microfluidic device, and a sample holder for securing the microfluidic device and aligning a region of the microfluidic device that includes the first chamber with the optical assembly.

In certain implementations, the systems further include a heating device placed adjacent to the microfluidic device. The heating device is configured to provide heat to the microfluidic device, a light source configured to provide excitation light to the liquid sample. The analyzer device is configured to run software that controls (i) an amount of heat provided by the heating device to the microfluidic device, and (ii) a magnitude of the excitation light provided by the light source to the microfluidic device.

In some implementations, the light source includes one or more light emitting diodes.

In some implementations, the analyzer device is configured to determine, based on processing the fluorescent signal, a clinical indicator associated with the detection of the target analyte. For example, the clinical indicator can be a level of a bacterial enzyme determined based on an intensity of the fluorescent signal.

In certain implementations, the systems include one or more interface electronics, and a control circuit connected to a headphone jack of the analyzer device and configured to transmit control signals to the one or more interface electronics. The analyzer device is configured to transmit signals to the control circuit through the headphone jack of the analyzer device.

In some implementations, the one or more lenses include a tube lens with a numerical aperture approximately equal to 0.4 and a focal length approximately equal to 3.3 millimeters, and an objective lens with a numerical aperture approximately equal to 0.79, a focal length approximately equal to 16 millimeters, and is coated with a 350 to 700 nanometer antireflective coating. In certain implementations, the emission filter includes a 500 nanometer long pass emission filter.

In another general aspect, the present disclosure features methods of performing a fluorometric assay using a portable system to detect a change in fluorescence intensity. In these methods the portable system includes at least a microfluidic device, an optical assembly, and an analyzer device. The methods include the operations of introducing a detection reagent and a liquid sample into the microfluidic device, and acquiring a fluorescence signal produced by a volume of the detection reagent and the liquid sample within the microfluidic device. The fluorescence signal represents the presence of the target analyte in the volume of the detection reagent and the liquid sample. The methods also include the operations of processing the fluorescence signal, and based on processing the fluorescence signal, determining a clinical indicator associated with the presence of the target analyte. The methods can further include the operation of providing the clinical indicator.

In some implementations, acquiring the fluorescence signal includes applying a plurality of excitation intensities to the volume of the detection reagent and the liquid sample within the microfluidic device. In certain implementations, the clinical indicator is a level of a bacterial enzyme determined based on an intensity of the fluorescent signal.

In some implementations, introducing the detection reagent and the liquid sample into the microfluidic device includes the operation of introducing, through an inlet of the microfluidic device, the liquid sample either before, during, or after introduction of the detection reagent through the inlet. The methods also include the operation of removing, from an outlet of the microfluidic device, a volume of the detection reagent and the liquid sample to cause a target analyte, if present, to be retained on a surface of a filter in the microfluidic device. The method also includes the operation of exposing the target analyte to the detection reagent specific to the target analyte.

In some implementations, the detection reagent includes beta-Lactamase Enzyme Activated Fluorophore (β-LEAF), and the target analyte is beta-lactamase produced by S.

*aureus*. In certain implementations, the target analyte, if present, is concentrated on a surface of a filter in the microfluidic device such that the concentration on the surface of the filter is greater than a concentration of the target analyte in the liquid sample. In some implementations, the liquid sample includes an antibiotic, the target pathogen is bacteria that is resistant to the antibiotic, and the clinical indicator is an indication of whether the target pathogen is present in liquid sample.

Advantages of the portable wide field systems and methods described herein include extensibility and the ability to reproduce many existing rapid tests that are presently performed in laboratories (e.g., glucose, gram stain, etc.). For example, due to the portability, the systems permit an operator to gather epidemiological information in a resource-limited field site for collection and aggregation in a centralized database without requiring network connectivity at the testing location. Additionally, due to the high testing speed and throughput, the systems can be used as a cost-effective alternative to traditional laboratory-based diagnostic techniques to identify AR prevalence, e.g., in resource-limited locations, where such laboratory-based techniques are often not suited for use. The detection of AR in resource-limited locations can also provide further downstream effects, such as the reduction of AR progression, promotion of responsible antibiotic use, and assistance in hospital referrals of AR cases. For example, ESBL can spread via plasmid-mediated processes, which often confer multi-drug resistance, so early detection of AR in resource-limited locations can improve various clinical outcomes in these regions by reducing multi-drug resistance.

Other versions include corresponding systems and apparatuses configured to perform the actions of the methods.

One or more implementations can include the following optional features. For example, in some implementations, the binding moieties are one or more different antibodies, and the ligands are one or more antigens to which the antibodies specifically bind.

As used herein, when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As described herein, spatially relative terms, such as "under," "below," "lower," "over," "upper" and the like, are used to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

As described herein, "liquid sample" can refer to any quantity of a liquid or fluid that contains, or is suspected of containing, one or more target pathogens. A liquid sample, for instance, can be extracted from a biological sample derived from humans, animals, plants, fungi, yeast, bacteria, tissue cultures or viral cultures, blood cultures (e.g., with or without antibiotics), throat swabs, or a combination of the above. In some instances, a liquid sample can include a bodily fluid, such as serum, serum, buffy coat, saliva, whole blood, partially processed blood, nasopharyngeal fluid (e.g., sinus drainage), wound exudates, pus, lung and other respiratory aspirates, bronchial lavage fluids, medial and inner ear aspirates, cyst aspirates, cerebrospinal fluid, stool, diarrheal fluid, tears, mammary secretions, ovarian contents, ascites fluid, mucous, gastric fluid, gastrointestinal contents, urethral discharge, peritoneal fluid, meconium, vaginal fluid or discharge, amniotic fluid, semen, penile discharge, synovial fluid, urine, sputum, seminal or lymph fluids, or the like. A liquid sample can be first processed (e.g., purified or partially purified) and/or mixed with buffers and/or reagents used to generate appropriate assay conditions.

As described herein, "subject" can refer to any warm-blooded organism including, but not limited to, human beings, pigs, rats, mice, dogs, goats, sheep, horses, monkeys, apes, rabbits, cattle, etc. The term "subject" can also be used interchangeably herein with the term "patient."

As described herein, "electrical communication" can refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component.

As described herein, "in fluid communication" can refer to a fluid (e.g., a liquid) that can move from one part of a device to another part of the device. Two or more parts of the device can be in fluid communication by being physically linked together or adjacent one another, or the fluid communication can be mediated through another part of the device.

As described herein, "coupled" can refer to direct coupling or indirect coupling via a separate object. The term can also encompass two or more components that are continuous with one another by virtue of each of the components being formed from the same piece of material. Also, the term "coupled" may include chemical, mechanical, thermal or electrical coupling. Fluid coupling can mean that fluid is in communication between designated parts or locations.

As described herein, "detection reagent," "fluorescent probe," "probe," "label," "tag," and "marker" can be used interchangeably and refer to a molecule or composition of molecules that is detectable by optical, spectroscopic, photochemical, biochemical, immunological, chemical, or magnetic means, and is typically bound or complexed with a target pathogen. Fluorescent probes can include, but are not limited to, colored, radioactive, fluorescent, ultraviolet, or magnetic molecules or particles capable of binding to a target analyte, e.g., proteins such as enzymes expressed by pathogens. The detection reagent or probe can also be conjugated to other molecules or particles (e.g., antibodies) that are known to bind to a target analyte. One example of a fluorescent probe is a fluorescence quenching-based probe, such as beta-Lactamase Enzyme Activated Fluorophore (beta-LEAF). The key point is that these probes are not fluorescent until activated, e.g., by cleavage, by a target analyte, such as an enzyme, e.g., beta-lactamase.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more implementations are set forth in the accompanying drawings and the description below. Other potential features and advantages will become apparent from the description, the drawings, and the claims.

BRIEF DESCRIPTION OF THE DRAWINGS

FIGS. 7A-D are schematic diagrams that illustrate an example of one implementation of the portable wide field fluorimeter system of FIG. 1A.

In the drawings, like reference numbers represent corresponding parts throughout.

DETAILED DESCRIPTION

In some implementations, the new portable wide field fluorimeter systems described herein can be used as low-cost mobile platforms to perform fluorometric assays to detect a change in fluorescence intensity in a liquid sample, for example caused by the presence of a target analyte, such as a protein, e.g., an enzyme, expressed by a pathogen, for example, in a point-of-care setting. The systems can use a detection reagent that includes a probe that is activated, e.g., become fluorescent, in the presence of a target analyte (e.g., enzymes expressed by antibiotic resistant bacteria that acti- vate the probe, e.g., by cleavage). Results of the fluorometric assay can be used to determine antibiotic susceptibility directly from patient samples over a short time period (e.g., less than 20 minutes). The systems can be designed to perform fluorometric assays in areas with limited healthcare infrastructure, such as field sites in LIMC.

The systems include a microfluidic device that processes a patient sample and a detection reagent specific to a target analyte, an analyzer device with an optical assembly to collect and process a fluorescence signal associated with the fluorometric assay, and interface electronics to provide fine-tuned control over signal detection and processing. In some implementations, the portable analyzer device can be a mobile device, such as a mobile phone, a tablet computing device, and/or a laptop computing device.

System Overview

Figure 1A:
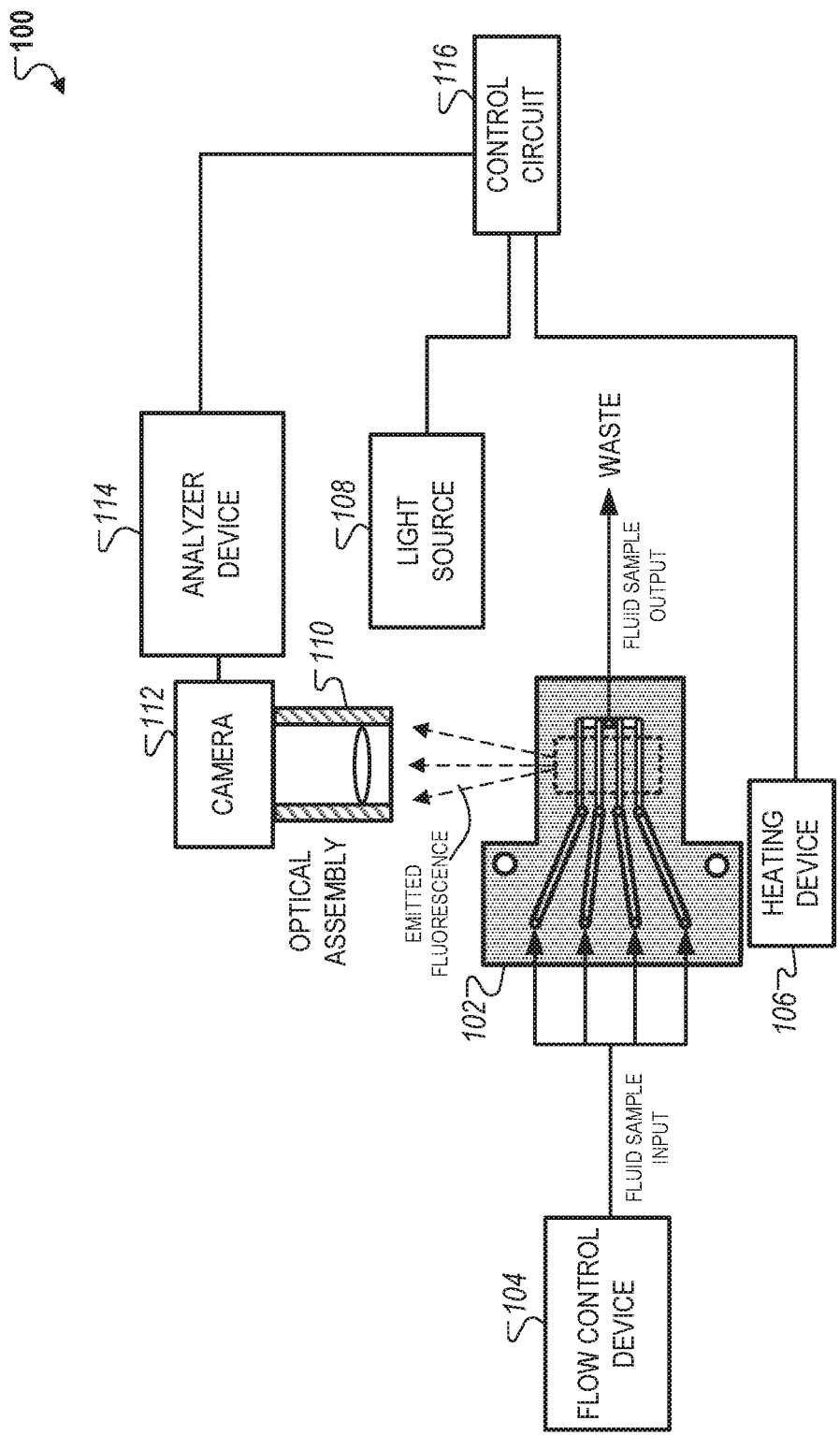
FIG. 1A is a block diagram that illustrates an example of a portable wide field fluorimeter system.

FIG. 1A is a block diagram that illustrates an example of a portable wide field fluorimeter system 100. The system 100 generally includes a microfluidic device 102, a flow control device 104, a heating device 106, a light source 108, an optical assembly 110, a camera 112, an analyzer device 114, and control circuit 116.

In general, the system 100 can be used to perform a portable fluorometric assay of a liquid sample to detect the presence of a target analyte, e.g., an enzyme expressed by a pathogen within the blood. A detection reagent, e.g., a fluorescent probe, is mixed with the liquid sample and used for detection of a target analyte that activates, e.g., cleaves, the probe causing the cleaved portions of the probe to fluoresce. The fluorescent signal can be detected by the camera 112 and processed by the analyzer device 114. The fluorescent signal is emitted when illuminated with excitation light provided by the light source 108.

In some implementations, the detection of the target analyte, e.g., an enzyme such as beta-lactamase, within the liquid sample can be used to identify whether a particular target pathogen is AR. For example, the liquid sample can be processed whole blood (e.g., whole blood with white blood cells removed), urine, cerebrospinal fluid, or any other fluid sample that may contain the target analyte and/or target pathogen. The target analyte, in these implementations, can be ESBL, and the detection reagent can be β-LEAF, which emits fluorescence once activated, e.g., cleaved, by any beta-lactamase in the sample fluid, and that can be used to characterize AR, as discussed in more detail below.

The microfluidic device 102 can be a cartridge that permits the flowing and processing of the liquid sample and the detection reagent (collectively referred to as "sample fluid") through a fluidic circuit to perform a fluorometric assay as described herein. The fluidic circuit of the microfluidic device 102 can include one or more inlets through which sample fluids are introduced into the microfluidic cartridge, one or more microfluidic channels and microfluidic chambers through which the sample fluids flow, and one or more outlets through which the sample fluids exit the chamber to a waste chamber or container. The structural aspects of the microfluidic device 102 and its fluidic circuit are discussed in more detail below with respect to FIGS. 2A-L.

The flow control device 104 can be any type of fluid delivery device used to introduce a sample fluid into a fluidic circuit. For instance, the flow control device 104 can be a peristaltic pump, a syringe pump, a pressure controller with a flow meter, or a pressure controller with a matrix valve. The flow control device 104 can be attached to tubing that attaches to the inlet port of the microfluidic device 102 to introduce the sample fluid into the channels of the microfluidic device 102. In some instances, the flow control device 104 is also capable of adjusting the flow rate of the sample fluids introduced into the microfluidic chamber according to a predetermined or user-adjusted program. This predetermined program is based on a specific sequence that involves flowing the liquid sample for a certain period of time at certain speeds and then introducing the detection reagent to label the target analyte for fluorescent detection.

The heating device 106 can be any type of device that supplies heat to maintain a certain temperature of the sample fluids that are introduced into the microfluidic device 102 while performing the fluorometric assay. For example, the heating device 106 can be a hot plate, a heating mantle, or a hot-tube furnace that is placed underneath the microfluidic device 102. In some implementations, the heating device 106 is contained within a housing that also includes other components of the system 100, such as the optical assembly 110, the camera 112, the analyzer device 114, the light source 108, and the control circuit 116. In such implementations, the heating device 106 and the other components of the system 100 can be integrated and/or self-contained within a single housing to increase portability of the system 100. In other implementations, the heating device 106 can be a separate off-the-shelf heating device that is placed underneath a housing that contains other components of the system 100.

The heating device 106 can be controlled to adjust the amount of heat that is supplied to the microfluidic device 102. For instance, the amount of heat provided to the microfluidic device 102 can be adjusted based on the type of fluorometric assay to be performed using the system 100. In some implementations, the heating device 106 is adjusted by a human operator (e.g., by manually adjusting a knob that controls power supplied to the heating device 106). In other implementations, the heating device 106 can be the controlled automatically by the control circuit 116, e.g., controlled by software that runs on the analyzer device 114.

The light source 108 can be used as a fluorescent pump source to illuminate the sample fluids within the microfluidic device 102 for detection of a fluorescence signal. The light source 108 can include one or more light emitting diodes (LEDs) or laser diodes. For example, the light source 108 can include a 470 nm LED with a plastic condenser and lens and includes a 460 nm to 480 nm band pass excitation filter. The light source 108 can be powered by batteries that are located within the housing of the system 100, or alternatively, powered by a power supply unit (not shown) that is connected to an electrical outlet. The light source 108 is oriented to emit fluorescent excitation light at a certain angle to the optical path between the lens of the camera 112 and the microfluidic device 102 that contains a sample to minimize excitation light contamination of the emission optical train within the optical assembly 110. For example, the light source 108 can be oriented to emit fluorescence excitation light at a 45 degree angle relative to the top surface of the microfluidic device 102. The light source 108 can be attached to a structure that arranges it relative to the microfluidic device 102. For example, in some implementations, the light source 018 is clamped to a cage system that is attached to a base plate (or sample holder) that holds the microfluidic device 102.

The optical assembly 110 includes components, such as lenses, filters, lens tubes, that allow the camera 112 to collect light corresponding to fluorescence emission by the detection reagent. For example, the optical assembly 110 can include two plastic lenses, an emission filter (e.g., 510 nm long pass filter) that are mounted in a lens tube. The optical assembly 110 can be attached to the camera 112 to create an optical path for light emitted by the detection reagent and to be collected by the camera 112. For example, the optical assembly 110 can be attached to a holder that secures the camera 112 so that the optical path within the lens tube of the optical assembly 110 is aligned with a sensor of the camera 112 for signal detection. The optical assembly 110 is discussed in greater detail below with respect to FIG. 3.

The optical assembly 110 can be used to improve light collection efficiency compared to light collection by the camera 112 alone. For example, the optical assembly 110 can include lens the focus the emitted fluorescence onto the image sensor of the camera 112 to increase light collection efficiency by, for example, a factor of 100.

The camera 112 can be any image capturing device that is capable of capturing images that represent a fluorescence signal produced by the detection reagent within the microfluidic device 102. In some implementations, the camera 112 is a camera of a mobile device, such as a mobile phone, a tablet computing device, or a laptop computing device (e.g., a back facing camera of a smartphone). Alternatively, in other implementations, the camera 112 is a dedicated active-pixel sensor (APS) having a photodetector and an integrated circuit for image capturing. For example, the camera 112 can be a dedicated image sensor that collects images that are then transmitted to the analyzer device 114.

The analyzer device 114 can be a computing device that is capable of acquiring, processing, and/or storing image data. For example, the analyzer device 114 can be a mobile phone, a tablet computing device, a laptop computing device, a palmtop computer, a smart wearable device, or any other device with processing capabilities. In some implementations, the camera 112 and the analyzer 114 are components of a single device, e.g., a smartphone camera that is attached to a smartphone. In such implementations, image data collected by the camera 112 can be accessed and stored directly by the analyzer device 114. Alternatively, in other implementations, the camera 112 can be discrete device that collects and transmits image data to the analyzer device 114 using a suitable wired connection, e.g., a universal serial bus (USB) connection, or a wireless connection, e.g., paired Bluetooth connection, near-field communication (NFC), etc. For example, the camera 112 can be a dedicated CMOS sensor that is connected through USB or wirelessly to an analyzer device 114 that is a laptop computing device.

The analyzer device 114 can include and run software that processes image data collected by the camera 112. For example, the analyzer device 114 can run image processing software that detects a change in fluorescence emitted from the liquid samples of the microfluidic device 102 over time to determine whether a target analyte and/or target pathogen is present. For example, the software can use a normalization curves for the detection reagent to identify a detected increase in fluorescence over specified time period after introducing the liquid sample and the detection reagent into the microfluidic device 102 as an indirect representation that the target pathogen is present within the liquid sample. As another example, the software can use the normalization curves to estimate a concentration of the target pathogen in the liquid sample based on the magnitude and/or the rate of increase of fluorescence signal over the specified period of time caused by the level of target analyte, e.g., enzyme expressed by the target pathogen. The fluorescent signals can be further processed to determine clinically relevant parameters, such as the AR to antibiotics associated with the target pathogen.

The control circuit 116 can include one or more circuits that are configured to receive signals from the analyzer device 114 to adjust the operation of electronics of the system 100. For example, the control circuit 116 can receive analog signals from the analyzer device 114 to adjust the power supply provide to the light source 108 and control the intensity of emission provided to the liquid sample in the microfluidic device 102. As another example, the control circuit 116 can receive analog signals from the analyzer device 114 to adjust the power supply to the heating device 106 and control the heat applied to the liquid sample within the microfluidic device 102. In other examples, the control circuit 116 can control other electronic devices of the system 100 that are not depicted in FIG. 1A, such as pumps associated with the flow control device 104, switches associated with the camera 112 that control image acquisition, among others. In these examples, different interface electronics can be controlled by the control circuit 116 using different multiple frequency signals.

The control circuit 116 can interface with the analyzer device 114 using a suitable communication protocol that permits the transmission of data and/or signals between electronic devices. For example, in some implementations, the control circuit 116 is connected to the analyzer device 114 through a headphone jack of the analyzer device 114.

In operation, the system 100 can be used to perform a fluorometric assay on a fluid introduced into the microfluidic device 102. The introduced fluid can contain a liquid sample collected from a human specimen, e.g., urine, CSF, processed whole blood, and a detection reagent that includes a fluorophore that emits fluorescence once activated by the target analyte. In some instances, the change in fluorescence over a period of time after the fluid is introduced into the microfluidic device 102 can be used to characterize AR. For example, the target analyte can be an enzyme that is produced by an antibiotic resistant bacterium so that a detected change in fluorescence can be used to determine that the patient may be infected with an antibiotic resistant bacteria.

In some instances, results of the fluorometric assay can be provided to an operator that uses the system 100 to perform the assay, e.g., by displaying the results on a display associated with the analyzer device 114 or by generating a printout of the results using an associated printing device. In other instances, the results can be transmitted to central data processing facility over a network, such as a wireless local area network (WLAN) or a wide area network (WAN) such as the Internet. The results can include, for instance, a graph of representing the detected changes in fluorescence for a liquid sample over a specified time period, e.g., 60-minutes. Alternatively, the results can include an indication as to whether a patient associated with the liquid sample is identified as being susceptible to AR based on the results of the fluorometric assay. For example, if a change in fluorescence is detected in a liquid sample over the time period during which the fluorometric assay is performed, then the patient can be identified as being susceptible to AR. In some implementations, the operator may be presented with different options, e.g., through a display of the analyzer device 114, to select an option for the amount and type of results to view, print, save, or edit.

Sample Preparation and Processing

Figure 1B:
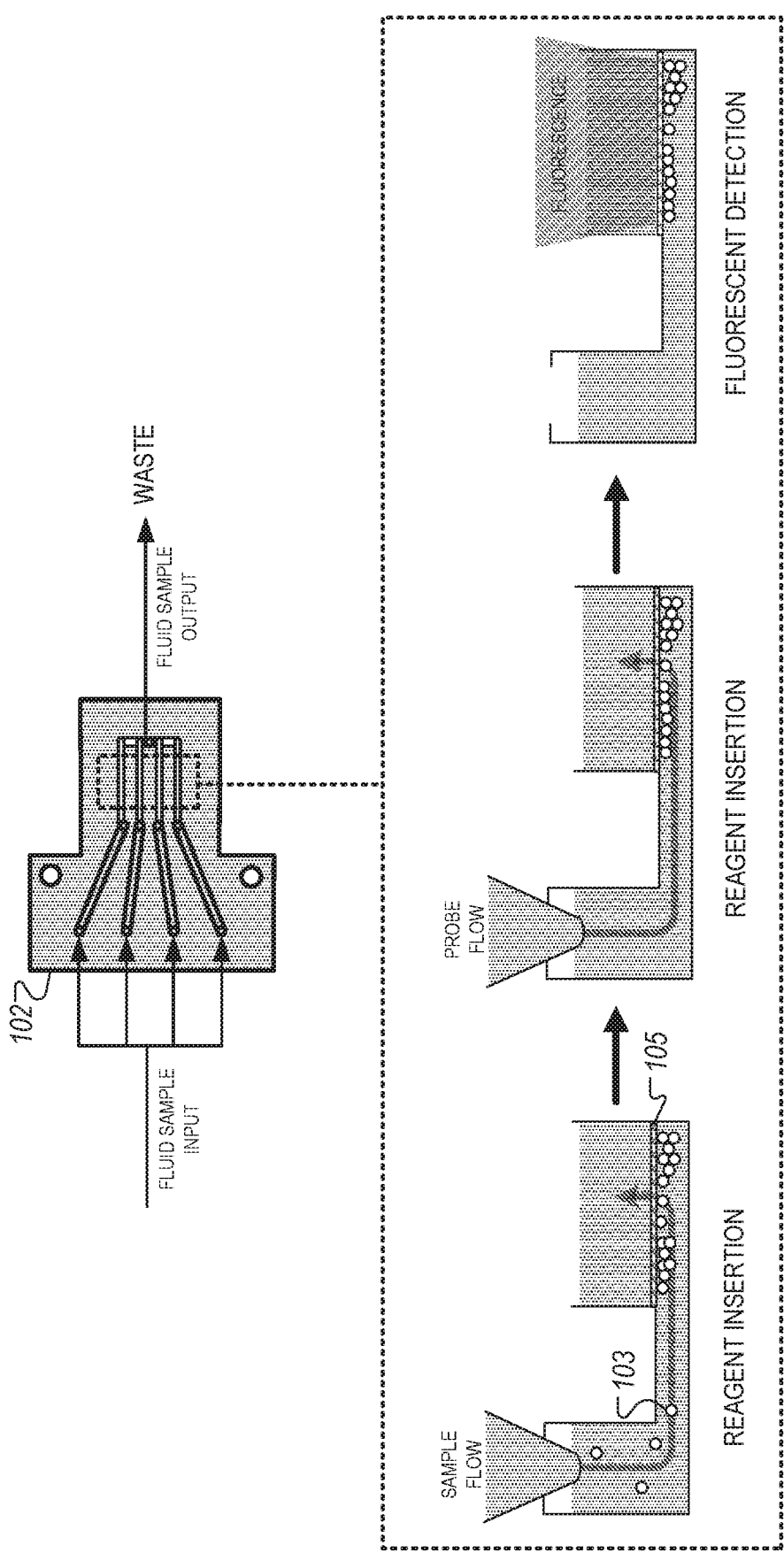
FIG. 1B is a conceptual diagram that illustrates sample processing in a microfluidic device of the portable wide field fluorimeter system of FIG. 1A.

FIG. 1B is a conceptual diagram that illustrates sample processing in the microfluidic device 102 of the system 100 of FIG. 1A. Although the microfluidic device 102 can be used with different types of liquid samples, examples of liquid samples referenced below are processed whole blood, urine, and cerebrospinal fluid that are collected from a subject that is a human patient. In other implementations, other types liquid samples collected from non-human subjects, such as primates and other animal models used in research, can also be evaluated using the techniques discussed below.

A liquid sample obtained from a subject is initially processed prior to being introduced into the microfluidic device 102. For example, whole blood can be centrifuged and filtered using a 5 μm filter to remove leukocytes prior to introduction into the microfluidic device 102. In other examples, the liquid sample can be obtained from storage (e.g., stored at 4° C. in laboratory storage facility) and transported to a testing site where the liquid sample is to be tested using the system 100.

In the example depicted in FIG. 1B, a volume of the processed liquid sample (e.g., 100 μL to 2 mL) is introduced and flowed through the microfluidic device 102. For example, the volume of the liquid sample can be injected into an inlet of a fluidic circuit of the microfluidic device 102 using a syringe pump that applies pressure to allow fluid to flow into the microfluidic device 102 at a specified flow rate for a specified period of time (e.g., 10 seconds). The applied pressure forces the volume of the liquid sample flow through channels of the fluidic circuit (which are depicted and discussed in more detail below with respect to FIGS. 2A-K).

As the liquid sample moves through the channel, target analytes associated with target pathogens 103 are trapped on a surface of an outlet filter 105. If whole blood is introduced into the microfluidic device 102, any red blood cells, for example, that are captured on the surface of the outlet filter 105, can be lysed by administering a lysing solution. The lysed cells can then be removed prior to performing the fluorometric assay.

A detection reagent specific to the target analyte associated with the target pathogen 103 can then be introduced into the microfluidic device 102 until the detection reagent contacts the target analyte directly and provide a detectable signal (e.g., fluorescence). For direct-binding detection reagents, excess/unbound probe can be washed off after this step. The unbound or unreacted detection reagent may reside between the outlet filter 105 and the bottom of the channel and thus provide a source of background interference during detection. To reduce background interference, the outlet filter 105 can be depressed towards a lower surface of the housing to displace any unbound or unreacted detection reagent. A photodetector (not shown) can then be used to detect the presence of the target analyte, and thus the presence of a target pathogen. The detected signal can be subsequently analyzed to provide information about the target pathogen (e.g., quantity).

In some implementations, the order of steps discussed above can be changed, or certain steps discussed above can be omitted depending upon the particular application of the fluorometric assay. For example, the liquid sample can be filtered to remove certain particles (e.g., red blood cells) prior to introduction into the microfluidic device 102. Alternatively, a lysing solution can be added to the liquid sample prior to introduction into the microfluidic device 102. In some instances, the detection reagent can be introduced into the microfluidic device 102 prior to introduction of liquid sample into the microfluidic device 102. In some other instances, the liquid sample and the detection reagent can be mixed prior to introduction into the microfluidic device 102.

For example, a mixture of the liquid sample and the detection reagent can be incubated for a specified time period prior to introduction into the microfluidic device 102.

Figures 1C, 1D:
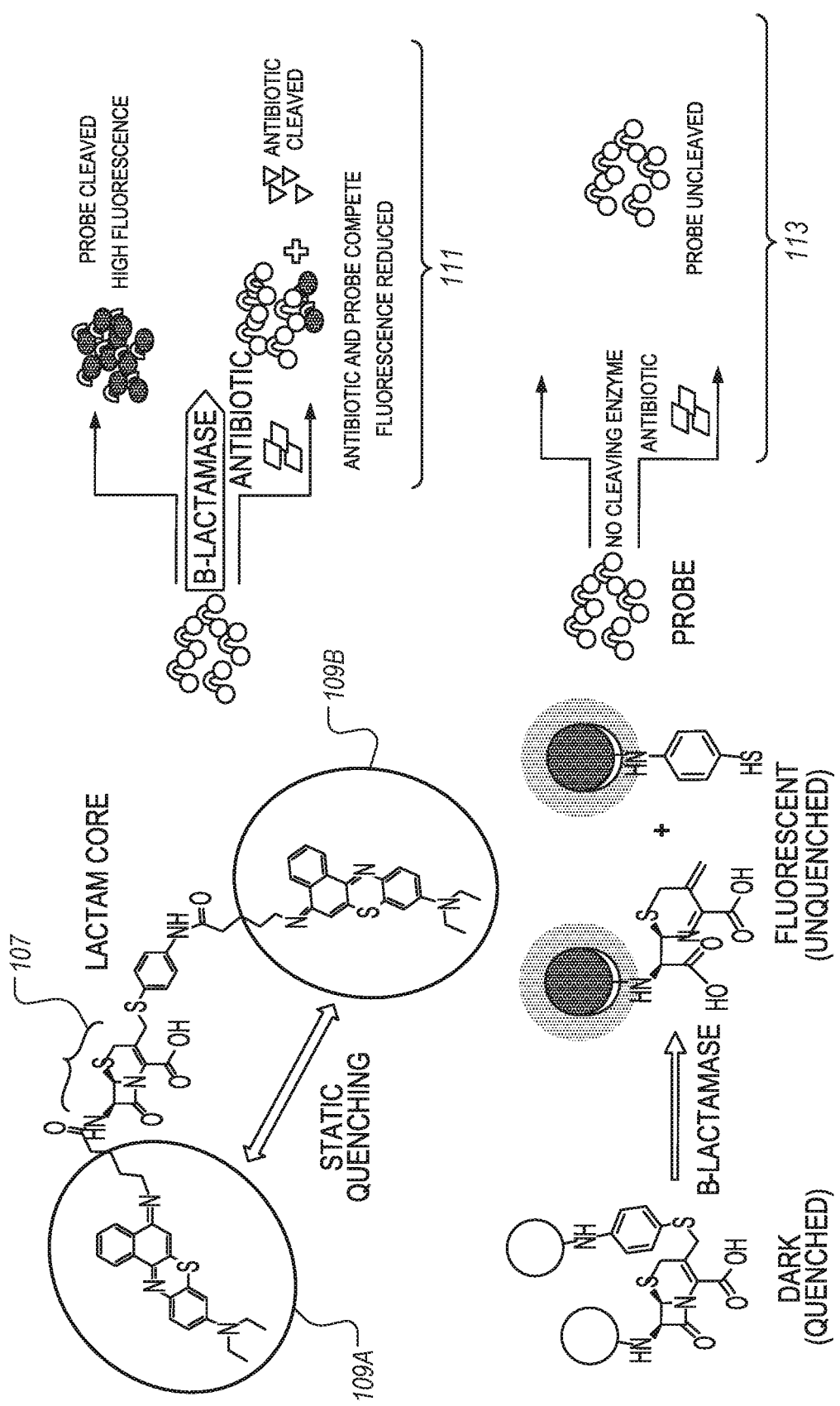
FIGS. 1C-D are conceptual diagrams that illustrate the principle of a β-lactamase enzyme activated fluorophore (β-LEAF) assay.

In some implementations, the technique depicted in FIG. 1B is used for performing a fluorometric assay using a fluorescence-activatable probe, such as β-lactamase enzyme activated fluorophore (β-LEAF). β-LEAF can be used be used to detect the presence of a target analyte, e.g., β-lactamase, produced by pathogenic bacteria, in a liquid sample based on detection of a fluorescence signal emitted by the β-LEAF that results from a reaction depicted in FIGS. 1C-D and discussed in more detail below.

A β-LEAF detection reagent can be prepared as follows. A chloro-group on 7-amino-3-chloromethyl-3-cephem-4-carboxylic acid p-methoxybenzyl ester is substituted with 4-aminothiophenol with the help of 4-methylmorpholine. A mixture of carboxylic acid-modified Bodipy-FL and O-(7-azabenzotriazole-1-yl)-N,N,N,N'-tetramethyluroniumhexafluorophosphate in dry N,N-dimethylformamide is then stirred for 30 minutes. This mixture is dissolved in a solvent mixture of trifluoroacetic acid: anisole: dichloromethane (DCM) and stirred at 0° C. for one hour. The solvent is removed under vacuum, and the residue was purified by high-performance liquid chromatography (HPLC). Diisopropylethylamine is then added to the stirring solution. The resulting reaction mixture is protected from light and stirred overnight. The solvent is removed under vacuum, and the residue is reconstituted in DCM. The organic layer is washed with brine. After removing the solvent under vacuum, a crude product was purified by HPLC to high purity (>95%). Concentrated stocks are then prepared in 100% DMSO and stored at −20° C.

In implementations where the microfluidic device 102 is used to perform a β-LEAF assay, the volume of the detection reagent that is introduced into the microfluidic device 102 is a 25 μl liquid sample of 10 μM β-LEAF in 10% DMSO with or without 25 mM antibiotic. Fluorescence is measured immediately after introduction of the detection reagent and then 10 minutes after insertion to determine the change in fluorescence observed between a first time point (e.g., immediately after introduction) and a second time point (e.g., 10 minutes after insertion). The two measurements can be used to represent a change in fluorescence between the first and second time points, which can then be used to estimate, for example, a concentration of a target analyte within the liquid sample.

FIGS. 1C-D are schematic diagrams that illustrate the principle of a β-LEAF assay. Referring initially to FIG. 1C, the chemical structure of a β-LEAF probe is depicted. The β-LEAF probe includes a β-lactam core structure that includes a cleavable lactam ring 107, flanked by two fluorophores 109A and 109B. The two fluorophores 109A, 109B undergo static quenching when the two fluorophores are in close proximity. To create this scenario, a cephalosporin β-lactam core can be modified such that the two fluorophores are anchored to opposite ends as shown in FIG. 1C. Consequently, the fluorophores are unable to emit fluorescence due to ground state interactions between each other. However, after probe cleavage by β-lactamase, the fluorophores diffuse away from each other, are no longer quenched, and thus regain their fluorescent properties. This results in a fluorescent signal that increases over time, and the slope of a graph of the results can be used as the readout for a β-LEAF assay. If the assay is repeated in the presence of a cleavable antibiotic that competes with the β-LEAF for β-lactamase cleavage, the rate of β-LEAF cleavage will decrease, resulting in no fluorescence increase.

To encapsulate the data, the suppression of fluorescence change (ΔFs) is defined as $(\Delta F_{BL} - \Delta F_{BL+antibiotic})/\Delta F_{BL}$, where $\Delta F_{BL}$ and $\Delta F_{BL+antibiotic}$ is the fluorescence rate of change of the β-lactamase only and β-lactamase and antibiotic conditions, respectively. A ΔFS approaching a value of 1 indicates that β-lactamase is not produced by a target pathogen, e.g., non-beta-lactamase producing bacteria. FIG. 1D illustrates two examples of fluorometric assays 111 and 113. The fluorometric assay 111 is performed on a liquid sample that includes pathogen that produces a cleaving enzyme, e.g., β-lacatamase. The fluorometric assay 113 is performed on a liquid sample that includes a pathogen that does not produce the cleaving enzyme.

As the fluorometric assay 111 is performed, β-lactamase producing pathogens (which are resistant to the antibiotic, because they cleave and destroy the antibiotic) cause β-lacatamase to compete with both the β-LEAF probe and the antibiotic for cleaving, which then reduces the fluorescence that is produced due to a lower number of uncleaved fluorophores present within a liquid sample that contains the β-lactamase producing pathogen, the antibiotic, and β-LEAF. As a result, the amount of fluorescence produced is reduced relative to a liquid sample that does not include the antibiotic.

Alternatively, as the fluorometric assay 113 is performed, because the target pathogen does not produce β-lactamase, there is no cleaving enzyme that can cleave the β-LEAF probe and the probe is left uncleaved. In this example, no fluorescence would be emitted since no cleaved probes (which emit fluorescence) are produced as a result of mixing a liquid sample and a detection reagent with the fluorescence probe.

Figure 8A:
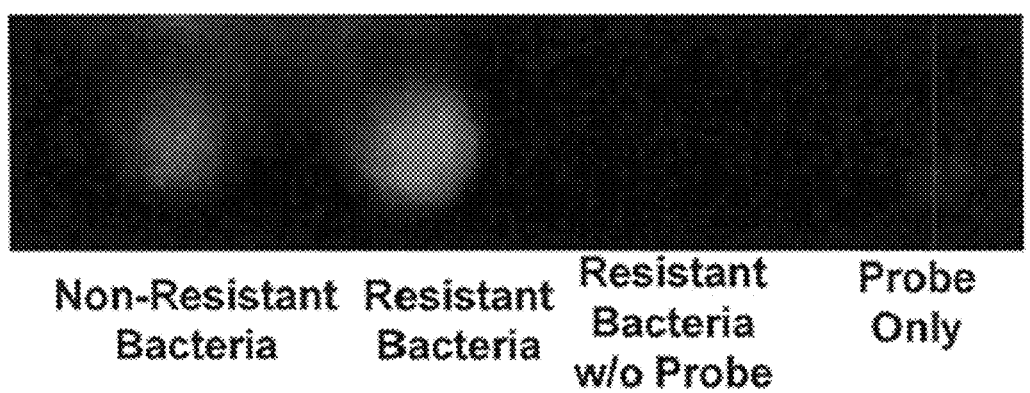
FIG. 8A is an image of the results of an experiment in which a fluorescence was detected by a portable wide field fluorimeter system.

With respect to the assay 111, the intensity of detected fluorescence can be used to identify AR susceptibility in a patient sample with respect to a selected antibiotic, i.e., whether the patient sample includes a pathogen that is resistant to the selected antibiotic. For example, as discussed in more detail below with respect to FIG. 8A, a fluorescence signal can be collected from liquid sample containing a fluorescent probe and a selected antibiotic. As shown in FIG. 8A, if the liquid sample includes bacteria that is resistant to the selected antibiotic, then the intensity of emitted fluorescence is greater than the intensity of fluorescence emitted a by fluid that includes the fluorescent probe, the selected antibiotic, and another liquid sample that includes non-resistant bacteria. In this example, a higher intensity fluorescence signal is detected for the fluid with the antibiotic resistant bacteria because the antibiotic is unable to inhibit the bacteria (which results in the production of cleaving enzymes that cleave the fluorescence probe for fluorescence emission). A lower intensity fluorescence signal is detected for the fluid with the non-resistant bacteria because the antibiotic inhibits the bacteria (which reduces the production of cleaving enzymes that cleave the fluorescent probe for fluorescence emission).

Microfluidic Device

Figure 2A:
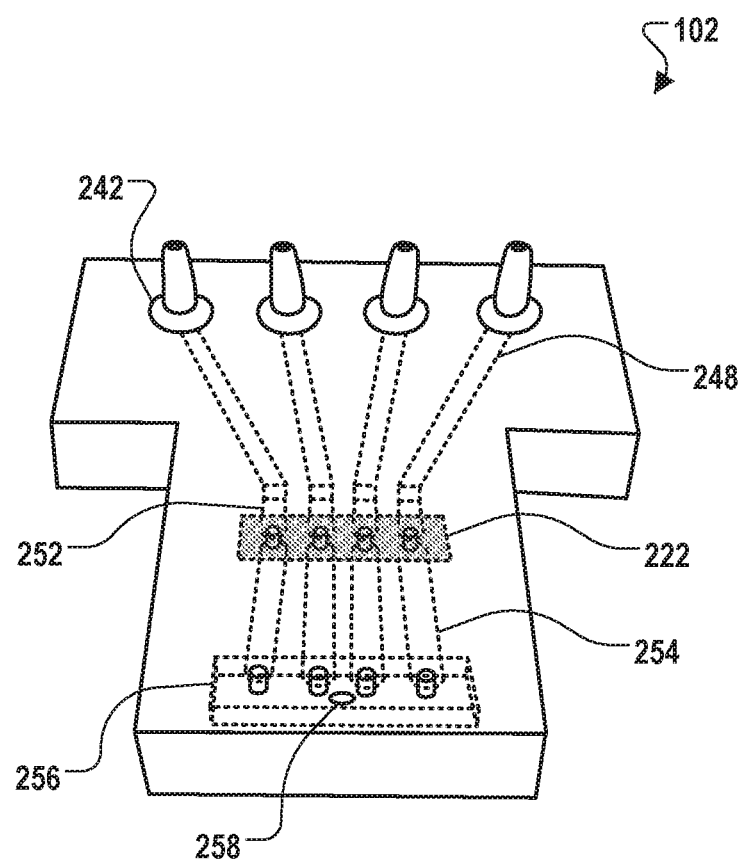
FIGS. 2A-L are schematic diagrams that illustrate examples of microfluidic devices that can be used with the portable wide filed fluorimeter system of FIG. 1A.

FIGS. 2A-K are schematic diagrams that illustrates an example of the microfluidic device 102 of the system 100 of FIG. 1A. Referring initially to FIG. 2A, a perspective view of the microfluidic device 102 is depicted. The microfluidic device 102 includes a housing with a fluidic circuit through which fluids (e.g., sample fluid, detection reagent) are flowed through and processed to perform a fluorometric assay as discussed throughout. The housing of the microfluidic device 102 can include one or more inlets 242 for receiving fluids, an outlet 258 for removing a volume of the fluid from the microfluidic device 102, a filter 222 associated with the outlet and being sized and dimensioned to retain a target pathogen and associated target analyte on a surface. In some instances, capture beads can be used to pull enzymes from the volume fluid in the microfluidic device 102.

As discussed herein, a "fluidic circuit" represents one or more channels, chambers, or holes within a housing of a microfluidic device that interconnect to form a generally closed microfluidic network. The microfluidic channels can include fluid passages having at least one internal cross-sectional dimension that is less than approximately 50 to 100 μm and/or a height or width of less than about 200, 100, or 50 μm. Such a microfluidic network may include one, two, or more openings at network termini, or intermediate to the network that interface with the external environment. Such openings may receive, store, and/or dispense a liquid. These dimensions provide various advantages such as improving the collection efficiency of target pathogens of a liquid sample within a chamber where the liquid sample is mixed with a detection reagent with a fluorescent probe, reducing liquid leaking from the fluidic chambers into other regions of the microfluidic device 102, ensuring that pressure resulting from liquid flow through the microfluidic chamber does not impact the structural integrity of the microfluidic device, among others.

Specifically, the microfluidic network can be sized and dimensioned so that target pathogens in a sample liquid can travel at a certain speed within the microfluidic channels to improve the likelihood of capture. The microfluidic device 102 can also include any other suitable features or mechanisms that contribute to liquid, reagent, and/or target pathogen manipulation or analysis. For example, the microfluidic device 102 may include regulatory or control mechanisms (e.g., valves and/or pumps) that determine aspects of liquid flow rate and/or path. Alternatively, or additionally, the microfluidic device 102 may be used with mechanisms (e.g., heaters, coolers, electrodes, lenses, gratings, light sources, pressure sensors, pressure transducers, microprocessors, microelectronics, etc.) that determine, regulate, and/or sense liquid temperature, fluid pressure, flow rate, exposure to light, exposure to electric fields, magnetic field strength, and/or the like. Furthermore, the microfluidic device 102 can include one or more features (e.g., any detectable shape or symbol, or set of shapes or symbols, such as black-and-white or colored barcode, a word, a number, and/or the like, that has a distinctive position, identity, and/or other property) that act as a code to identify a particular target analyte and/or target pathogen.

Figure 2B:
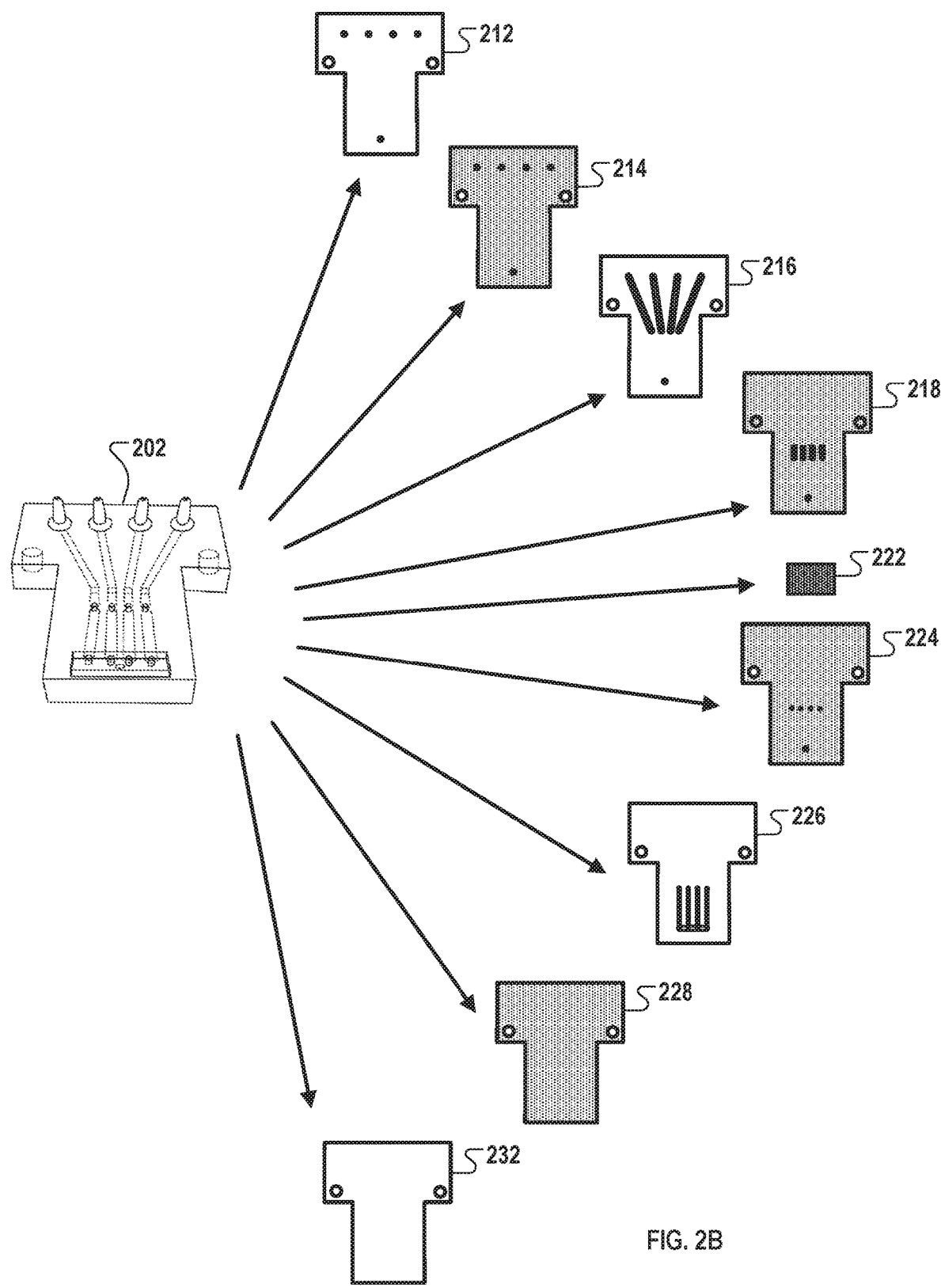

The housing of the microfluidic device 102 can include any one or combination of structures configured to, at least partially, enclose the device components. For example, the housing can include several separate components that are attached to one another (e.g., as depicted in FIG. 2B), or alternatively, can be formed as a unitary structure. The housing can include a solid, semi-solid, or flexible substrate made from one or a combination of materials having sufficient physical strength, and being capable of being shaped into a desired physical and functional appearance. In one example, the housing can be made from one or a combination of materials including, but not limited to, silicon, silicon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, super-alloys, zircaloy, steel, gold, silver, copper, tungsten, molybdeumn, tantalum, nickel-cobalt ferrous alloy KOVAR®), para-aramid synthetic fiber (e.g., KEVLAR®), polyimide film (e.g., KAPTON®), biaxially-oriented polyethylene terephthalate (e.g., MYLAR®), brass, sapphire, etc.

The material(s) used for the housing can be sufficiently robust to facilitate storage, transport, and use of the microfluidic device 102. In some instances, the material(s) used to form the housing can be compatible with reagents associated with use of the microfluidic device 102. For example, if any reagents are prearranged in the microfluidic device 102, the material(s) can be compatible with the reagents so that the reagents cannot dissolve, react with, or diffuse into the material(s) within a predetermined period of time.

The substrate including the housing of the microfluidic device 102 can be configured to handle a single liquid sample that may contain a plurality of target analytes and/or target pathogens. That is, a single liquid sample can be added to the microfluidic device 102 and the sample may be either aliquoted for parallel processing for detection of the target analytes, or the sample may be processed serially, with individual target analytes being detected in a serial fashion. In addition, liquid samples may be removed periodically or from different locations for in-line sampling. In other instances, the substrate including the housing can be configured for handling multiple liquid samples, each of which may contain one or more target analytes. In such instances, each liquid sample can be handled individually. For example, the manipulations and analyses can be performed. In parallel, with no contact or contamination between them. Alternatively, there may be some steps in common. For example, it may be desirable to process different liquid samples separately but detect all of the target analytes on the same portion of the microfluidic device 102 and/or at the same time.

The microfluidic device 102 can have a single or multiple fluidic circuits that are each separate from one another (i.e., each fluidic circuit is not in fluid communication with one another although they are included in the same housing). In the examples depicted in FIGS. 2A-J, the microfluidic device 102 includes four fluidic circuits, although in other implementations, the microfluidic device 102 can have greater than, or less than, four fluidic circuits. For example, the microfluidic device 102 can have a single fluidic circuit for performing a single fluorometric assay. In other examples, where the microfluidic device 102 has multiple fluidic circuits, each fluidic circuit can be used to perform a different type of fluorometric assay with a single microfluidic device. For instance, as depicted in FIG. 8A, each fluidic circuit can be used to perform a fluorometric assay on a different type of liquid sample (e.g., a liquid sample with non-resistant bacteria, a liquid sample with resistant bacteria, a liquid sample with resistant bacteria and no detection reagent, and a liquid sample without bacteria and a probe only).

Each fluidic circuit of the microfluidic device can include the features that permit fluid flow through the microfluidic device 102. The inlet 242 is sized and dimensioned to receive a liquid sample. The inlet 242 can be defined by one or more side walls that define an interior or lumen and an opening. In the example depicted in FIGS. 2A-J, the inlet 242 is defined by cylindrical interior, although any suitable cross-sectional profile, such as a rectangular cross-sectional profile, can also be used. The inlet 242 can include a membrane or septum that partitions the ambient environment from an interior of the outlet and prevents unwanted material (e.g., dust) from entering the microfluidic device 102.

The outlet 258 is sized and dimensioned to permit removal of a volume of the liquid sample from the microfluidic device 102. The outlet 258 can be spaced apart from the inlet 242 and in communication with channels and chambers of the fluidic circuit, e.g., channel 248, chamber 252, channel 254. The outlet 258 can be defined by one or more side walls that defined an interior or lumen of a hole on the surface of the microfluidic device 102. In one example, the outlet 258 can include a single side wall that defines a cylindrical interior or lumen. The outlet 258 can have an opening through which liquid is partly or entirely removed from the microfluidic device 102. The outlet 258 can have a circular cross-sectional profile, although other cross-sectional profiles can also be used. The dimensions of the outlet 258 can be the same as or different than the dimensions of the inlet 242. The outlet 258 can include a vacuum gasket that partitions the ambient environment from an interior of the outlet 258. The vacuum gasket permits a vacuum seal to be created within the outlet 258 while also preventing unwanted material (e.g., dust) from entering the microfluidic device 102.

The fluidic circuit of the microfluidic device 102 also includes channels 248, 254 in fluid communication with the inlet 242, the outlet 258, and a release mechanism associated with the flow control device 104. Each channel can include any suitable path, passage, or duct through, over or along which materials (e.g., liquid, target analytes, and/or reagents) can pass through the fluidic circuit of the microfluidic device 102. Each channel can have any suitable dimensions and geometry, including width, height, length, and/or cross-sectional profile, among others, and may follow any suitable path, including linear, circular, and/or curvilinear, among others. Each channel can also have any suitable surface contour, including recesses, protrusions, and/or apertures, and may have zany suitable surface chemistry or permeability at any appropriate position within the channel. Each channel can branch, join, and/or dead-end to form any suitable network. Accordingly, a channel can function in target analyte and/or target pathogen positioning, sorting, retention, treatment, detection, propagation, storage, mixing and/or release, among others.

A filter 222 can be placed between the top and bottoms halves of the chamber 252 to capture the target entity by permitting the flow of sample fluid through the filter 222 between the channel 248 and the channel 254, but prevent the passage of the target analyte and/or target pathogen. In this respect, target analytes present within a liquid sample can be captured in the chamber 252 and used for fluorescence detection. For example, the filter 222 can have a pore size that is large enough to permit liquid to pass, but smaller than an average diameter of the target analyte and/or target pathogen and/or a biomolecule associated with the target pathogen and used for fluorescence detection, and therefore prevents passage of a pathogen or target analyte into an interior of the chamber 252 that is opposite to the surface of the filter 222 in contact with the target pathogen and in connection with the channels 254. For example, the filter pore size can range from pore size between 10 nm and 0.5 microns.

In one example, the diameters of the channels 248, 254 can be less than about 100-90 microns, about 80-90 microns, about 70-80 microns, about 60-70 microns, about 50-60 microns, or less than 50 microns, e.g., about 40-50 microns, about 30-40 microns, about 20-30 microns, about 10-20 microns. The diameter of each channel can be uniform across its length or may vary at one or more locations. In another example, a portion of the channels 248, 254 extending between a lower surface of the filter 222 and a lower surface of the chamber 252 can have a diameter less than about 50 microns to minimize the amount of unreacted detection reagent available to create background interference during detection, e.g., about 90-100 microns, about 80-90 microns, about 70-80 microns, about 60-70 microns, about 50-60 microns, about 40-50 microns, about 30-40 microns, about 20-30 microns, about 10-20 microns, or about 5-10 microns. Moreover, the diameter of the channel 248, 254 and the chamber 252 can be shaped and designed to reduce the volume of unbound or unreacted detection reagent(s) probed by a detector.

Advantageously, the chamber 252 can be sized and dimensioned to minimize the amount of unreacted detection reagent available to create background interference during fluorescence detection, which can be used to improve the sensitivity of the microfluidic device 102. This advantage can be readily apparent considering conventional techniques used to reduce background when the detection signal is fixed. Confocal microscopy, for example, involves raster scanning of a focused point and refocusing that point virtually through a pinhole to remove background, and total internal reflection microscopy (or TIRF) focuses a laser at a critical angle onto a glass coverslip to create a very thin (e.g., 100 nm) layer of light. Additionally, nanoscale chambers are fashioned out of a flexible polymer, which is then placed over a single molecule of interest and sealed. Confocal microscopy and IMF fall under the class of "optical sectioning," where the background is removed by using, optics to probe only a thin area of interest. Fashioning, nanoscale chambers out of a flexible polymer employ a specific geometry, but with a flexible or deformable chamber that is adapted to the random positions of the pathogen. The chamber 252 discussed herein, conversely, provides a fixed geometry that advantageously reduces background while allowing sample preparation simultaneously without optical sectioning or deformable chambers.

In some implementations, a portion or all of the fluidic circuit of the microfluidic device 102 can be coated with one or more detection reagents. The detection reagents that are coated on surfaces of the fluidic circuit can be the same or different than the detection reagent that is mixed into the fluid sample used for fluorescence signal detection (e.g., a detection reagent that includes a fluorescent probe that is cleaved by an enzyme produced by a target pathogen in a liquid sample). As an example, a portion of the wall(s) defining the inlet 242 can be coated with one or more detection reagents that improve the capture of the target pathogen within the fluidic circuit of the microfluidic device 102. In another example, a portion of the wall(s) defining the outlet 258 can be coated with such one or more detection reagents. In yet another example, all or only a portion of the walks) defining the channels 248, 254 and the chamber 252 can be coated with such one or more detection reagents.

In some instances, the detection reagent used for the fluorometric assays described herein can be combined with a slow-release compound or polymer (e.g., poly(lactic-co-glycolic acid)). In such instances, the resultant slow-release detection reagent can be flowed through the fluidic circuit of the microfluidic device 102 and then lyophilized to coat a portion or the entirety of the fluidic circuit. Other methods of coating can include spin-coating with drying and/or aerosolization processes. In this regard, coatings can be applied to certain components or features of the microfluidic device 102 prior to assembly, e.g., so only certain parts of the fluidic circuit are coated.

In some instances, a filter associated with the inlet 242 can be coated with a slow-release detection reagent as described above. In such instances, the slow-release detection reagent can be attached to the inlet filter as described above or, alternatively, the detection reagent may be integrated into beads made of a slow-release compound or polymer (e.g., polylactic-co-glycolic acid), which are placed onto the inlet filter. As a liquid sample is flowed through the inlet 242, the beads are designed to dissolve and thereby release the detection reagent into the liquid sample.

Coating one or more portions of the microfluidic device 102 with one or more detection reagents can be used to provide several advantages. First, very high concentrations of detection reagent(s) can be obtained for the same amount of detection reagent(s) (as opposed to directly mixing the detection agent(s) with the liquid sample) because the volume of the fluidic circuit is very small. Such high concentrations can improve the limit of detection. Second, the fact that the detection reagent(s) is/are coated onto the microfluidic device 102, as opposed to adding the detection reagent(s) with the liquid sample, creates a "single-step" process whereby only the liquid sample is added to the microfluidic device 102. In addition to improved user convenience, this reduces user-induced variation and error, which are the largest sources of diagnostic uncertainty.

In another aspect, the microfluidic device 102 can additionally or optionally include a release mechanism that is coupled to the housing and in fluid communication with the fluidic circuit of the microfluidic device 102. Advantageously, the release mechanism can be configured to permit selective release of a retained target analyte and/or target pathogen from a surface of the filter 222. Release of the retained target analyte and/or target pathogen from the surface of the filter 222, which can be source of background interference during detection, minimizes interference (e.g., auto-fluorescence) and improves sensitivity of the microfluidic device 102 by moving the retained target analyte and/or target pathogen to an area of relatively low background interference. The release mechanism can generally include any one or combination of structures, components, or elements that enable movement of a retained target analyte and/or target pathogen away from a preselected site/area (e.g., the filter 222) by removing, overcoming, and/or rendering ineffective the force(s) that retains the target analyte and/or target pathogen. After release, the target analyte and/or target pathogen may have any suitable destination within the fluidic circuit that improves target analyte and/or target pathogen detection.

The structures, components, or elements of the release mechanism can be configured for precise control of the retained target analyte and/or target pathogen within the fluidic circuit. Such structures, elements, or components may be controllable by tactile, electronic and/or robotic means, and may be connected (e.g., directly connected) to the housing. In one example, the release mechanism can include a plug member (not shown) that is slidably disposed within a second outlet (now shown) of the housing. When disposed in the second outlet, the plug, member provides a retaining force on flow of the liquid sample through the fluidic circuit. The position of the liquid sample within the fluidic circuit can be precisely controlled by manipulating the plug member within the second outlet. By moving the plug member axially away from the housing, for example, the liquid sample can flow through the channel 254 towards the release mechanism and thereby move the retained pathogen off of the filter 222. In one example, the plug member can include a set screw. In another example, the release mechanism can include a syringe (not shown) that is capable of being fluidly coupled to the outlet 258 or the second outlet of the microfluidic device 102.

In instances where the microfluidic device 102 does not include a release mechanism, a suction or a vacuum (e.g., from a syringe) can be selectively applied (e.g., fluidly coupled) to the outlet 2580 (or a second outlet) to remove the retained pathogen from the filter 222.

The microfluidic device 102 can include other features to facilitate ease of use and improve target pathogen detection. For example, the microfluidic device 102 can include one or more fluid reservoirs (not shown), such as a suitable receptacle or chamber for storing materials (e.g., reagents) before, during, between, and/or after target pathogen detection. Such reservoirs may include input, intermediate, and/or output reservoirs. Input reservoirs may store materials prior to inputting the liquid sample into the microfluidic device 102. By contrast, intermediate reservoirs may store materials during and/or between uses of the microfluidic device 102. Finally, output reservoirs may store materials prior to outputting from the microfluidic device 102, for example, to an external processor or waste, or prior to disposal of the device. Additionally, reagents may be dried onto the wall(s) defining each of the channels 248, 254, the chamber 252, the inlet 242, the outlet 258, and/or a second outlet.

Referring now to the example depicted in FIG. 2A, four inlets 242 are depicted for exemplary purposes. In other implementations, a larger or smaller number of inlets can be present on the microfluidic device 102. For example, in other implementations, the microfluidic device 102 can include a fluidic circuit that includes a single inlet 242 that is in fluid connection with a single channel 248. In such implementations, a single chamber 254 is formed and divided by the filter 222, such that a single channel 254 is connected to the chamber 256. In other implementations, the microfluidic device 102 can have greater than, or less than, four separate fluidic channels as shown in FIGS. 2A-J. In such implementations where the microfluidic device 102 includes multiple fluidic circuits, each fluidic circuit can be used to perform a different fluorometric assay. For example, as shown with the results depicted in FIG. 8A, each of the four channels can be used to test a different liquid sample (e.g., a liquid sample with a detection reagent and non-resistant bacteria, a liquid sample with a detection reagent and resistant bacteria, a liquid sample with bacteria but no probe, and a liquid sample with a detection reagent but no bacteria).

In the example depicted in FIG. 2A, the device includes structures attached to each of the four inlets 242. Such structures can then be attached to tubing to create a seal for fluid communication between the flow control device 104 and the fluidic circuit of the microfluidic device 102. For example, in one particular implementation, the structures can be rubber disk septa that are attached to the inlet 242 with a cyanoacrylate adhesive such as Loctite® 401 (Henkey Corp.; Rocky Hill, Conn.). In another particular implementation, the structures attached to the inlets 242 can be tubing that is inserted with an interference fit into the inlets 242. For example, the tubing can be stainless steel tubing with silicone tubing placed over the steel tubing and sealed with adhesive.

In some other implementations, the inlet 242 can be a hole in a housing that is connected to a channel of the fluidic circuit. In such implementations, a portion of a fluid delivery device, such as the tip of a syringe, can be inserted into the hole to create a seal for introducing a fluid sample into the fluidic circuit of the microfluidic device 102.

Microfluidic Device Fabrication

FIG. 2B illustrates an example of an implementation of a microfluidic device 202 that is assembled using multiple different layers 212, 214, 216, 218, 224, 226, 228, and 232. Except where described below, the microfluidic device 202 can be identically constructed and used as discussed above in reference to the microfluidic device 102. In the implementation depicted in FIG. 2B, the microfluidic device 202 is constructed by assembling each of the different layers to form a unitary housing. In this implementation, the assembly of the multiple layers forms the structures and features of the fluidic circuit of the microfluidic device 202.

In other implementations, a microfluidic device can be constructed using alternative device fabrication techniques. For example, the features and structures of fluidic circuit can be formed without the use of multiple layers as shown in FIG. 2B. In such implementations, suitable fabrication techniques can depend on the choice of substrate, but suitable methods can include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques. In addition, printing techniques can be used for the creation of desired fluid guiding pathways. For example, patterns of printed material can permit directional fluid transport. Thus, the build-up "ink" can serve to define a flow channel. In addition, the use of different "inks" or "pastes" can allow different portions of channels of the fluidic circuit having different flow properties. In other implementations, the devices can be generated using additive manufacturing techniques, such as is used in the semiconductor chip industry, or 3D printing.

In the example depicted in FIG. 2B, the microfluidic device 202 is constructed such that, when assembled, the layer 212 forms the top of the microfluidic device 202 and the layer 232 represents the bottom of the microfluidic device 202. In this example, layers 212, 216, 226, and 232 are made of, for example, a plastic such as an acrylic or polycarbonate material, and the layers 214, 218, 224, and 228 are double-sided adhesive (e.g., a thin plastic film with adhesive on both sides or a thin layer of adhesive of a specified thickness). The materials can be cut using, for instance, laser, e.g., a 50 W $CO_2$ laser. The filter 222 can be a membrane filter with a pore size between 10 nm and 0.5 microns, e.g., 25, 50, 75, 100, 200, 250, 300, 400, or 500 nm. The filter 222 can be made of a material that permits liquid to flow through the membrane, but prevents passage of target analytes and/or target pathogens. For example, the filter 222 can be made from a polycarbonate material, or alternatively, an oxide material, such as an $Al_2O_3$ filter membrane with 0.2 micron pores, that can be used with higher liquid flow rates.

In some instances, the filter 222 can be biologically inert and inert to improve capture of the target pathogen within a sample chamber used to perform a fluorometric assay. In some implementations, the filter 222 is naturally transparent, which can increase the amount of background fluorescence in a captured image due to fluorescence emitted by fluid that is on an opposite side of the surface of the filter 222 that faces a camera used for collecting emitted fluorescence. In some instances, the height of the bottom portion of the chamber 252 (e.g., the bottom portion 252B) can be reduced to minimize the volume of fluid that occupies the bottom region 252B (and thereby reduce background fluorescence). In other instances, the background fluorescence problem can be addressed by rendering the filter 222 opaque to limit the detection of fluorescence emitted by the volume of liquid through the filter 222. For example, the filter 222 can be rendered opaque using electroless nickel deposition without affecting, for instance, flow properties or biological inertness of the filter 222.

In one particular implementation, the layers 212, 216, 226, and 232 are 1/16" clear acrylic, e.g., from McMaster-Carr (Princeton, N.J. USA). In this implementation, the layers 214, 218, 224, and 228 are double-sided film adhesive 3M 8212 (3M; St. Paul, Minn.) with approximately a 100-micron thickness, which is selected to suppress background fluorescence and also avoid liquid clogging within the fluidic circuit.

During assembly of the microfluidic device 202, pressure is applied to the layers 212, 214, 216, 218, 224, 226, 228 to firmly seal acrylic layers with the double-sided adhesive layers. For example, the microfluidic device 202 can be assembled manually by hand by aligning each of the layers 212, 214, 216, 218, 224, 226, 228 on top of one another. In other examples, the microfluidic device 202 can also be assembled automatically using any suitable robotic means that automatically (e.g., without human input) align each of the layers 212, 214, 216, 218, 224, 226, 228 and apply pressure for construct the microfluidic device 202. FIGS. 2C-J depict each of the layers 212, 214, 216, 218, 224, 226, 228 in greater detail.

Figure 2C:
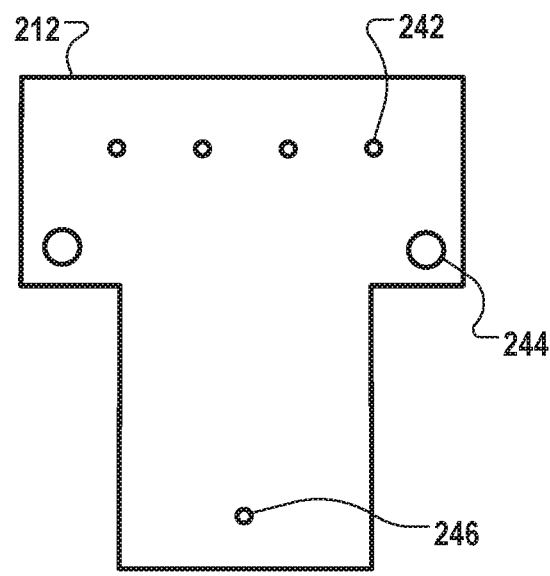
Figure 2D:
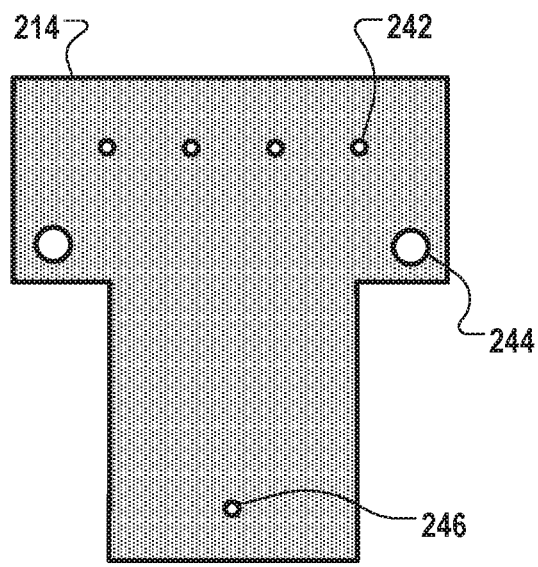

FIG. 2C illustrates an example of the layer 212. For example, the layer 212 can be formed from acrylic and includes four inlets 252, an outlet 246, and two alignment holes 244. The alignment holes 244 can be used to verify visually that individual layers are aligned with one another during assembly as discussed above. FIG. 2D illustrates an example of the layer 214. In this example, the layer 214 is formed from a double-sided adhesive and includes four inlets 242, the outlet 246, and two alignment holes 244.

Figure 2E:
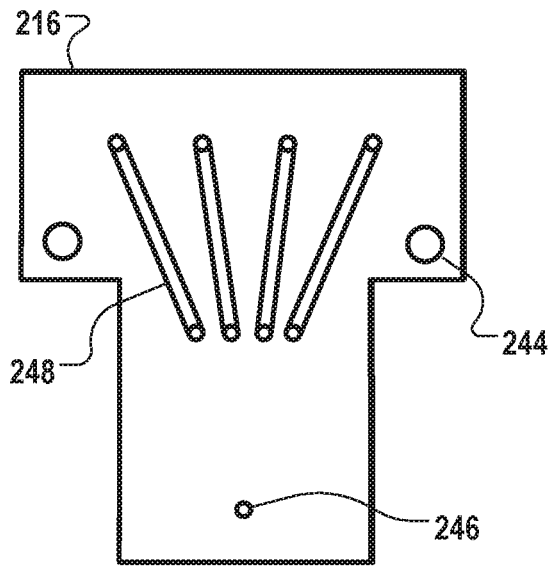

FIG. 2E illustrates an example of the layer 216. In this example, the layer 216 is formed from acrylic and includes four channels 248 that are interconnected with the four inlets 248 when the layer 216 is placed underneath the layer 214. The layer 216 also includes the outlet 246, and two alignment holes 244.

Figure 2F:
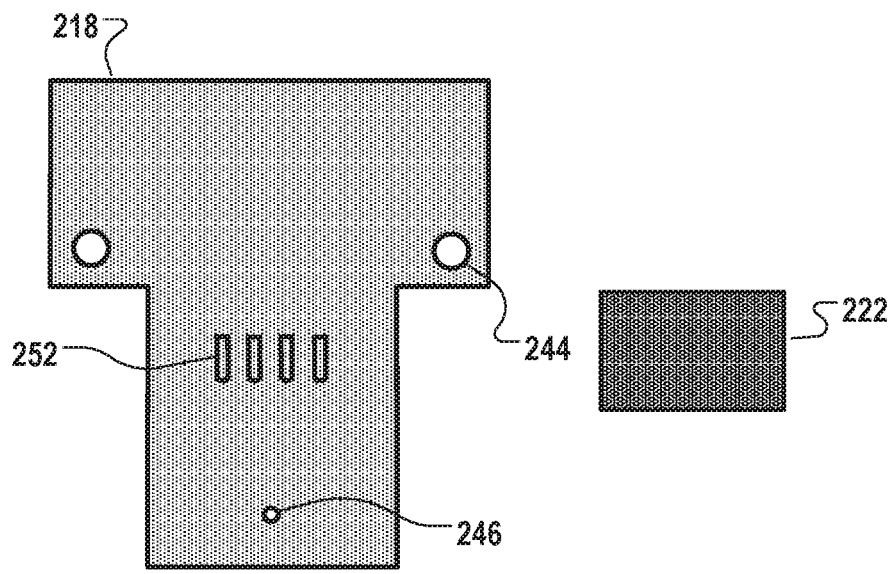

FIG. 2F illustrates an example of the layer 218. In this example, the layer 218 is formed from double-sided adhesive and includes four chambers 252 that are interconnected with the four channels 248 when the layer 218 is placed underneath the layer 216. The layer 218 also includes the outlet 246, and two alignment holes 244. The layer 218 is placed on top of the filter 222 such that the surface of the filter 22 cover an interior area formed by the recesses corresponding to the four chambers 252. As discussed above, the filter 222 permits fluids, such as a detection reagent and portions of a liquid sample, to pass through the top half of the chambers 252 to the bottom half of the chambers 252 (underneath the filter 222 in the layer 224) but prevents a target analyte and/or target pathogen from passing through the filter 222. The collected target analyte and/or target pathogen in the top half of the chamber 252 (on top of the filter 222) is then used for fluorescence detection.

Figure 2G:
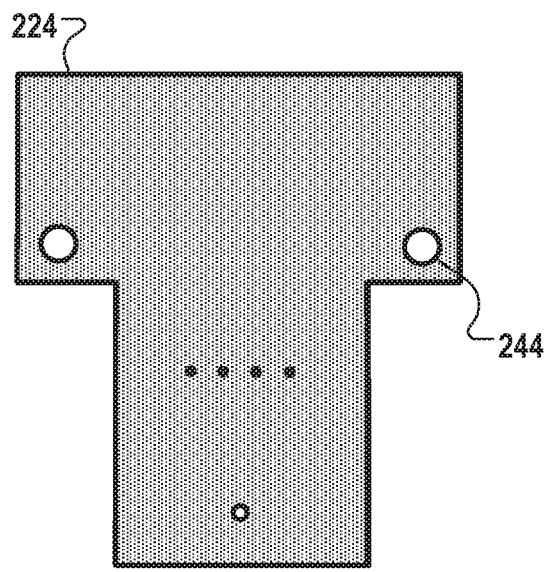

FIG. 2G illustrates an example of the layer 224. In this example, the layer 224 is formed from double-sided adhesive and includes four exit points that interconnect with the four chambers 252 of the layer 218 when the layer 224 is placed underneath the layer 218. The layer 224 also includes the outlet 246, and two alignment holes 244.

Figure 2H:
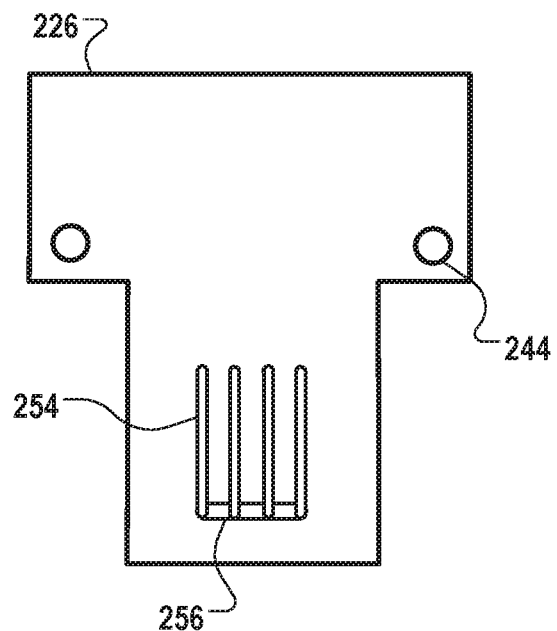

FIG. 2H illustrates an example of the layer 226. In this example, the layer 226 is formed from acrylic and includes four channels 254 that interconnect with the four exit points of layer 224 when the layer 226 is placed underneath the layer 224. The layer 226 also includes the chamber 256, and two alignment holes 244.

Figure 2I:
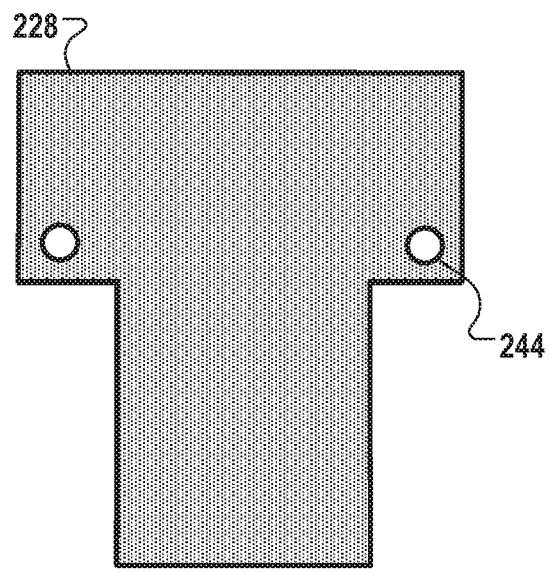
Figure 2J:
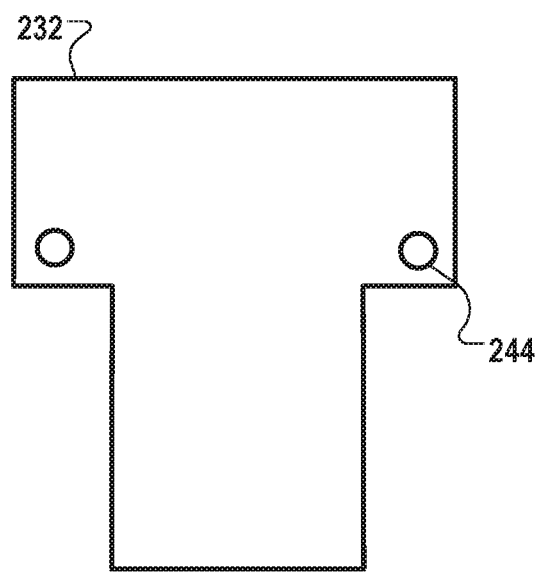

FIGS. 2I and 2J illustrates examples of the layers 226 and 232, respectively. In these examples, the layer 228 is formed from double-sided adhesive and the layer 232 is formed from acrylic. The layers 228 and 232 provide structural support to the microfluidic device 102 after assembly. For example, the layer 228 is applied as an adhesive that attaches the layers 226 and 232. Because the layers 228 and 232 are used for structural support, these layers do not include features or structures of the fluidic circuit of the microfluidic device 202. The layers 228 and 232 each have two alignment holes 244.

Figure 2K:
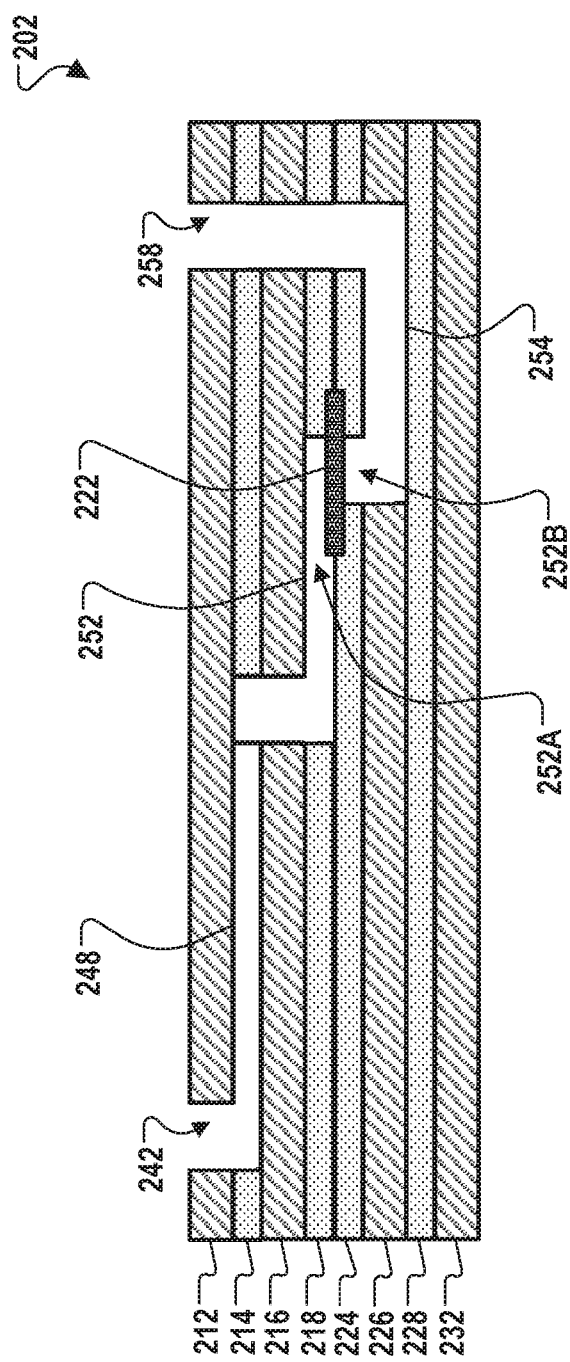

FIG. 2K is a schematic diagram that illustrates an example of a cross-sectional view of the microfluidic chip 202. As discussed above, the microfluidic device 202 includes multiple layers that are placed on top of one another to form the structures and features of the fluidic circuit of the microfluidic chip 202 within a housing. For instance, acrylic layers are attached to one another using double-sided adhesive layers. As examples, acrylic layers 212 and 216 are attached to one another using the layer 214, acrylic layers 216 and 226 are attached to one another using layers 218 and 224, and layers 226 and 232 are attached to one another using the layer 228. Assembly of the microfluidic device 202 in this manner can be used to reduce fluid leakage through the fluidic circuit of the microfluidic device 202.

As shown in FIG. 2K, the fluidic circuit of the microfluidic device 202 has a volume that is defined by structures and features such as the inlet 242, the channel 248, the chamber 252, the channel 254, and the outlet 258. A single channel is depicted in FIG. 2K for simplicity, although the microfluidic device 202 can also have multiple channels, e.g., four channels as depicted in FIG. 2B. As discussed above, fluids (e.g., liquid sample, detection reagent, etc.) are introduced into the microfluidic device 102 through the inlet 242. The fluids are then flowed through the channel 248 and collected in the chamber 252. The chamber 252 includes a top portion 252A above a top surface of the filter 222, and a bottom portion 252B below a bottom surface of the filter 222. The chamber 252 is formed by placing the filter 222 between the layers 218 and 224 in a specific region such that the filter 222 covers the entirety of the interconnection between the top portion 252A and the bottom portion 252B of the chamber 252. For example, the filter 222 can be sized and dimensions such that it covers the entire interior area of the holes of the layer 222 as depicted in FIG. 2A.

Once fluids that are collected in the chamber 252, the filter 222 permits passage of liquid, but prevents the passage of certain cells and the target analytes and/or target pathogens. For example, the filter 222 can be a membrane filter with pores that are sized, e.g., 0.2 microns, to be smaller the average size of the target pathogen so that reagents can flow through the filter 222 into the bottom portion 252B, but the target pathogen is collected in the top portion 252A. A volume of the fluids that can pass through the filter 222 then flows into the channel 254 towards the outlet 258. In some implementations, where the microfluidic device 202 includes multiple channels within a single housing, as is the case with the examples depicted in FIGS. 2A-J, the fluidic circuit can include a collection chamber (e.g., the chamber 256 as depicted in FIG. 2A) that collects fluid that flows from each channel. In such implementations, a volume of liquid that accumulates in the collection chamber exits the fluidic circuit through the outlet 258.

Figure 2L:
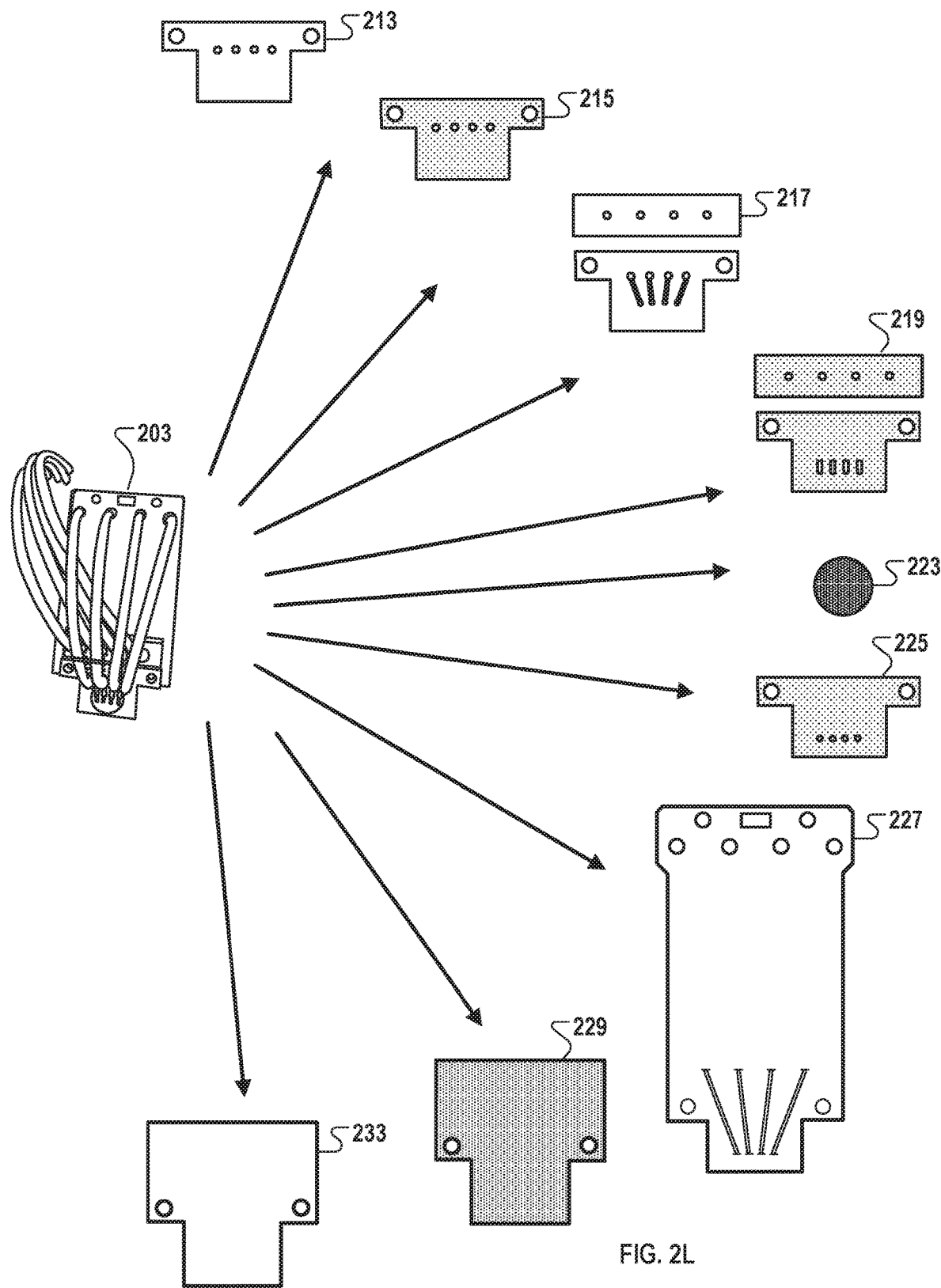

FIG. 2L illustrates an example of an implementation of a microfluidic device 203 that is assembled using multiple different layers 213, 215, 217, 219, 225, 227, 229, and 233. Except where described below, the microfluidic device 203 can be identically constructed and used as discussed above in reference to the microfluidic devices 102, 202. Additionally, the layers that make up the microfluidic device 203 can have the same dimensions (e.g., thickness) as the layers of the microfluidic device 202. The size and dimensions of the features and structures of the fluidic circuit in the microfluidic device 203 can also resemble that of the fluidic circuit of the microfluidic device 202 discussed above.

In the implementation depicted in FIG. 2L, the microfluidic device 203 is constructed by assembling each of the different layers to form a unitary housing. In this implementation, the assembly of the multiple layers forms the structures and features of the fluidic circuit of the microfluidic device 203. The microfluidic device 203 is constructed such that, when assembled, the top of the layer 213 is the top of the microfluidic device 203 and the bottom of the layer 233 is the bottom of the microfluidic device 203. In this example, layers 213, 217, 227, and 233 are made of, for example, a plastic such as an acrylic or polycarbonate material, and the layers 215, 219, 225, and 229 are double-sided adhesive (e.g., a thin plastic film with adhesive on both sides or a thin layer of adhesive of a specified thickness). The materials can be cut using, for instance, laser, e.g., a 50 W $CO_2$ laser in a similar manner as discussed above. The filter 223 can be a membrane filter with a pore size between 10 nm and 0.5 microns, e.g., 25, 50, 75, 100, 200, 250, 300, 400, or 500 nm. The filter 223 can be made of the same material as the material of the filter 222 as discussed above.

The design of the microfluidic device 203 can provide several advantages over the design of the microfluidic devices 102 and 103. For example, instead of tubing can be attached to the inlets of the fluidic circuit to allow the introduction of liquid samples from a container placed away from the microfluidic chamber (as depicted in FIG. 7E). As another example, the acrylic layers of the microfluidic layers can have slits nearby interconnections of different components of the fluidic circuit of the microfluidic device 203. For instance, the bottom portion of the layer 217 and the layer 227, which each have four channels, can have slits etched nearby inlets and outlets such that a laminating force that is applied on liquid that flows between layers (e.g., fluid entering the channels of the layer 218 through the holes of layer 213) is reduced to prevent fluid leaking at high pressures. The slits can be partially etched into the layers (e.g., they are not entirely cut through the body of each layer) so that they can be used for sealing and containment of channel pressure. In one implementation, slits are etched on the bottom of layer 217 (e.g., the surface that is attached to the layer 219) and on the top of layer 227 (e.g., the surface that is attached to the layer 225).

As another example of an advantageous design, layers 217 and 219 have split portions to relieve strain due to finite thickness of the filter 223 that is placed between layers 219 and 225. This ensures that the filter 223 can have any arbitrary thickness without risking failure due to risk of leakage. For example, without the separation of layers 217 and 219 as shown in FIG. 2L, thicker membranes, when used with the microfluidic device 203 can create a higher risk of fluid leakage due to increased strain the layers 219 and 225.

During a typical operation, the bottom of the microfluidic device 203 (e.g., the side that includes channels of the layer 227) is aligned with a camera for imaging. For example, as discussed above, a volume of liquid that occupies the chamber of the layer 219 after a liquid sample and a detection reagent has been mixed prior to, during, or after introduction into the microfluidic device 203 can be image. As discussed above, the filter 223 allows for the capture of a target pathogen (and in some instances, a target analyte such as a cleaving enzyme) in the chamber of the layer 225 while liquid is capable of passing through the chamber and entering the channels of the layer 227. The liquid that enters these channels then travel up the towards the outlet (which is interconnected to the top of the channels of the layer 227). Instead of collecting fluid that exits the fluidic circuit of the microfluidic chamber into a collection chamber, as discussed above for microfluidic devices 102 and 202, the volume of fluid exiting the outlets of each individual chamber instead flow through a separate tubing for each channel. This design allows the independent collection of fluid that exits each fluidic circuit that is included in the microfluidic device 203 (e.g., collecting four different waste liquids for each of the four fluidic circuits that are illustrated in FIG. 2L).

Figure 3:
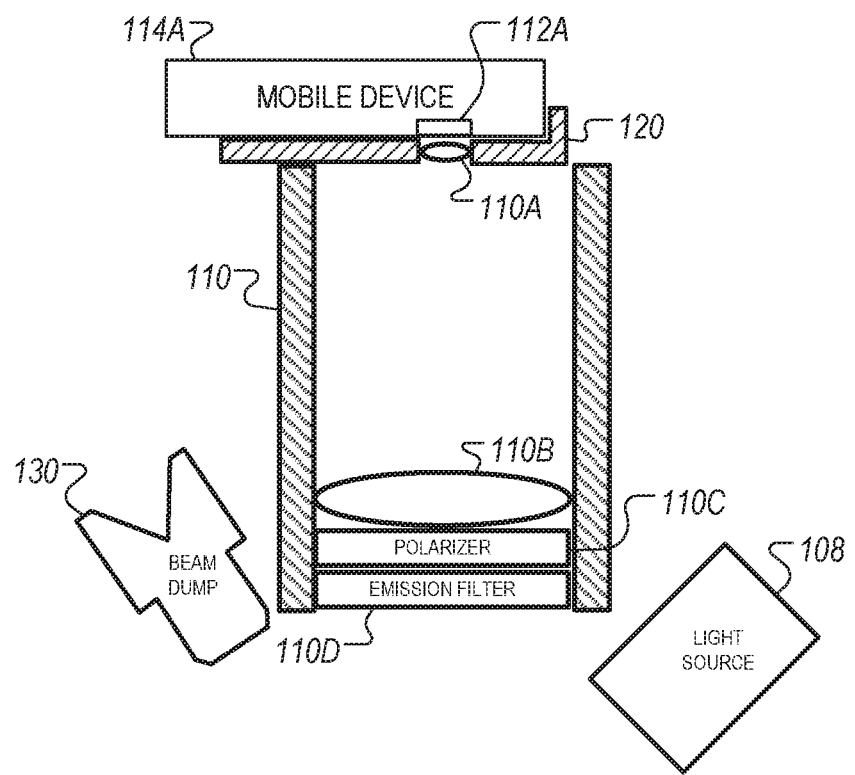
FIG. 3 is a schematic diagram that illustrates an example of an optical layout of components associated with an optical assembly of the portable wide field fluorimeter system of FIG. 1A.

FIG. 3 is a schematic diagram that illustrates an example of an optical layout of components associated with the optical assembly 110 of the system 100 of FIG. 1A. In this example, a mobile device 114A is used as the analyzer device 114 and an integrated camera 112A of the mobile device 114A is used as the camera 112. The mobile device 114A can be any suitable computing device that is capable of acquiring image data. For example, the mobile device 114A can be a mobile phone, a smartphone, a tablet computing device, a PDA, a laptop computing device, or a wearable device.

The mobile device 114A, in some instances, can include capabilities such as data processing, data storage, and image processing and analysis. For example, the mobile device 114A can be a smartphone that runs software on a mobile operating system and is capable of run native applications with certain functionalities on the mobile operating system. In this example, software running on the mobile device 114A can automatically perform image analysis application that processes images collected by the camera 112A to generate a fluorescence readout without requiring, for example, any additional computing devices to identify a clinically relevant parameter, e.g., AR susceptibility, based on a detected fluorescence signal.

In other instances, the mobile device 114A can have limited processing capabilities such that it only operates to collect and transmit image data captured by the camera 112A. For example, the mobile device 114A can be a cell phone that has basic communication features, e.g., network connectivity over a cellular network, but is not capable of running native applications. In this example, the mobile device 114A can transmit image data captured by the camera 112A to another computing device for image processing and analysis. For instance, the mobile device 114A can transmit the collected image data to an image processing server over a cellular-based network. The image processing server can then perform image processing and analysis to generate fluorescent readout and identify a clinically relevant parameter based on a detected fluorescence signal.

In the example depicted in FIG. 3, the mobile device 114A is secured to a holder 120 that allows the camera 112A to be aligned with the optical assembly 110 to create an optical light path for detecting fluorescence emitted from a liquid sample. The holder 120 can be constructed from any suitable rigid material, e.g., plastic, metal, etc., such that the mobile device 114A can be positioned in the holder 120. For example, the holder 120 can be a clamp that aligns the camera 112A of the mobile device 114A to a lens 110A of the optical assembly. As another example, the holder 120 can be an off-the-shelf phone case that is manufactured for the device type of the mobile device 114A and is modified to include a means for attaching the optical assembly 110 to align the lens 110A and the camera 112A, e.g., a threaded extension that allows the lens tube of the optical assembly 110 to be screwed onto the holder 120.

The optical assembly 110 includes two lenses 110A and 110B, a polarizer 110C, and an emission filter 110D. As discussed above, the components of the optical assembly 110 are used to create an optical light path that amplifies a fluorescence signal that is detected by the camera 112A. Additionally, the optical assembly 110 can be used to increase the numerical aperture for light collection relative to the numerical aperture of the camera 112A without the optical assembly 110.

The lens 110A can be a tube lens with a short focal length and placed flush against the camera 112A so that the camera 112A is set to an infinite working distance. The lens 110B can be an object lens that collects light from a sample and has a longer working distance and wide field ability (e.g., 110 $mm^2$) compared to the lens 110A. The emission filter 110D can be used to select certain wavelengths of light that pass through the emission optical train and for collection by the camera 112A. The polarizer 110C can optionally be used to convert a beam of light of undefined or mixed polarization into a beam of well-defined polarization (i.e., polarized light). A beam dump 130 can be used to reduce reflections of excitation light provided by the light source 108 within a housing of the system 100. The beam dump 130 can be arranged relative to the optical assembly 110 and the light source 108 to minimize high intensity reflections that can contaminate the optical emission path through the optical assembly 110. For example, in some instances, the beam dump 130 is arranged 45 degrees relative to a top surface of the microfluidic device 102 that contains a liquid sample to be imaged. The beam dump 130 can be a cone beam dump, or alternatively, any other suitable shaped beam dump (e.g., horn shape, baffles, etc.).

In one particular implementation, the lenses 110A and 110B are mounted within a 1" diameter lens tube. In this implementation, the lens 110A is a tube lens with a focal length of approximately 3.3 mm and a numerical aperture of approximately 0.4, and the lens 110B is an objective lens with a focal length of approximately 16 mm, a numerical aperture of approximately 0.79, and 350-700 nm antireflective coating. Additionally, in this implementation, the emission filter 110D is 500-510 nm long pass emission filter. The distance between the lens 110A and the lens 110B is approximately 6.75 mm, and the distance between the lens 110B and its focal plane (e.g., a plane that includes the liquid sample) is approximately 76 mm.

Figure 4A:
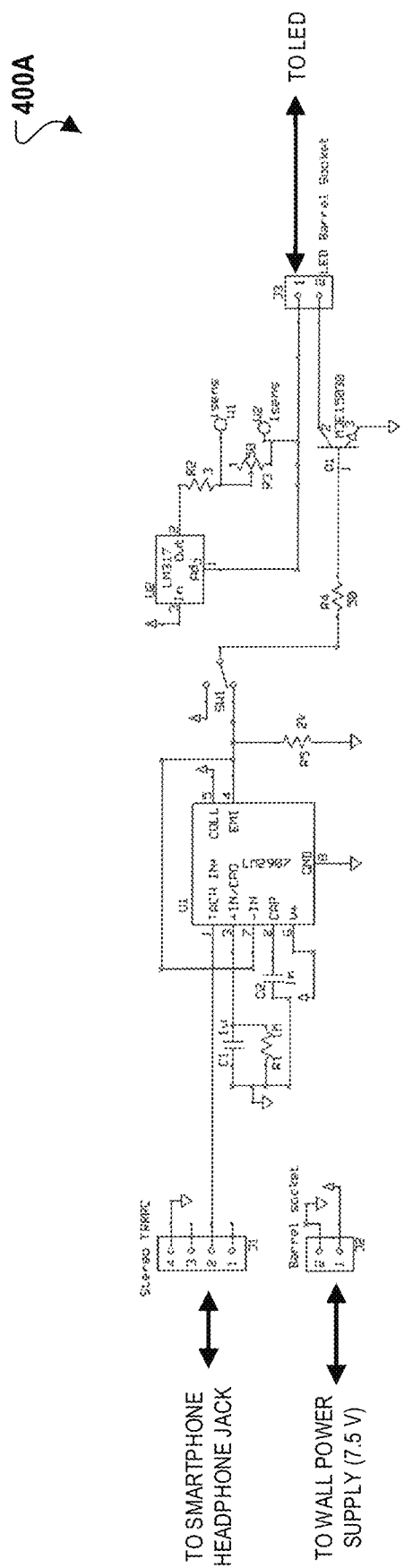
FIGS. 4A-C are circuit diagrams for examples of circuits that can be used to control interface electronics of the portable wide field fluorimeter system of FIG. 1A.
Figure 4B:
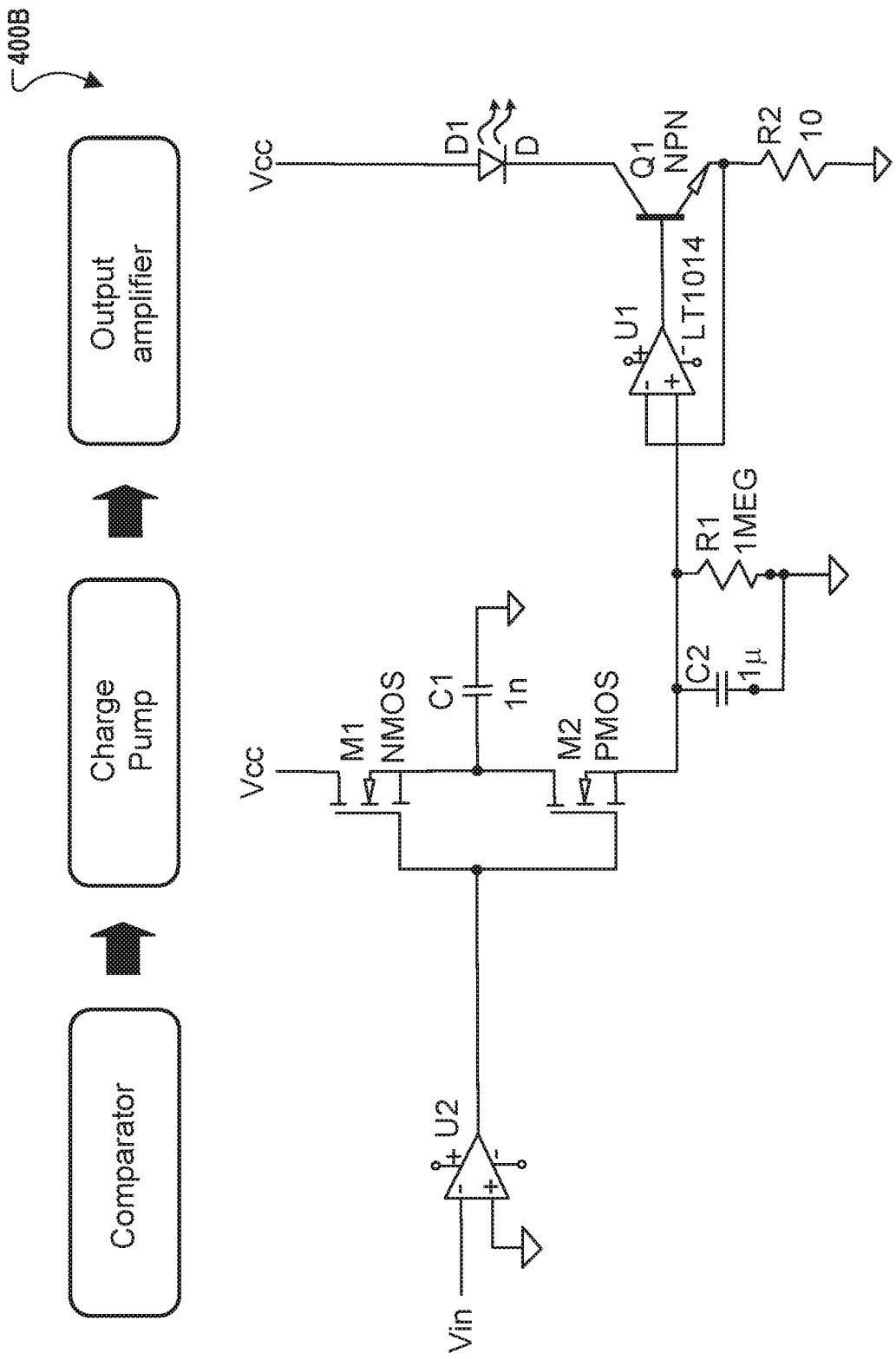
Figure 4C:
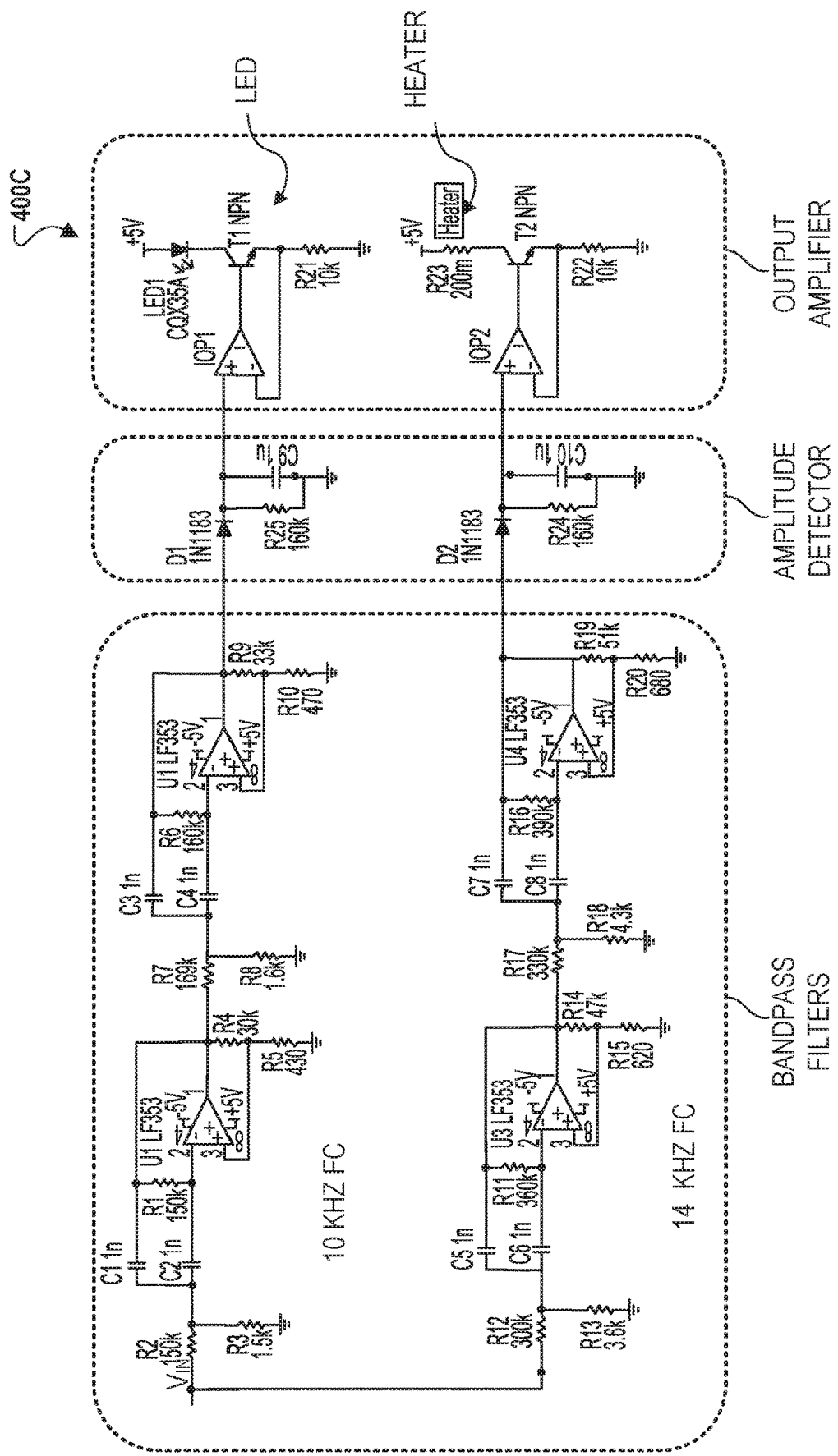

FIGS. 4A-C are circuit diagrams for examples of control circuits 400A-C, respectively, that can be used to control interface electronics of the portable wide field fluorimeter of FIG. 1A. Referring initially to FIG. 4A, a circuit diagram of a circuit 400A that is used to control the light source 108 is depicted. The circuit 400A can be implemented on a printed circuit board of the control circuit 116.

In the example depicted in FIG. 4A, the circuit 400A includes a 5-volt barrel socket that receives a power from a power supply, such as a 7.5-volt wall power supply. The circuit 400A also includes a communication module (e.g., stereo TRRRC) that is connected to, for instance, a headphone jack of the analyzer device 114 to receive analog control signals. Analog control signals received from the analyzer device 114 are processed by the circuit 400A and used to adjust the amount of power supplied to the light source 108. In particular, the circuit 400A includes an LED barrel socket that adjusts the power supplied to the LED to control excitation of a liquid sample while performing a fluorometric assay.

FIG. 4B shows a circuit diagram for a circuit 400B that is used for frequency control of the light source 108. The circuit 400B can be implemented on a printed circuit board of the control circuit 116. The circuit 400B can be used to control the intensity of excitation light provided by the light source 108 using, for instance, a headphone jack of the analyzer device 114. In some other instances, a similar signal control scheme can be used to control other interface electronics of the system 100, such as the heating device 106, the flow control device 104, motors, Peltier coolers, or any other voltage/current sources. In one implementation, this is accomplished by converting an output frequency of a signal provided by the analyzer device 114 to a voltage that is proportional to the excitation intensity of light output by the light source 108. In this implementation, because the output of the headphone jack of the analyzer device 114 is a stereo signal that has two outputs (e.g., an audio output for left ear and audio output for the right ear), each output can be used to control a different light source so that two light sources can be controlled based on a signal output signal transmitted through the headphone jack of the analyzer device 114.

Alternatively, in the example shown in FIG. 4B, the circuit 400B can be used to adjust the excitation intensity of the light output by the light source 108. The circuit 400B includes a comparator that converts a sine wave of an output signal from the analyzer device 114 and generates a square wave, and a charge pump that generates a voltage proportional to the frequency of light output by the light source 108 based on the square wave. The circuit 400B also includes an output amplifier that amplifies the voltage generated by the charge pump and generates an output signal that is used to control the light source 108. In some instances, the output amplifier of the circuit 400B can be used to control other interface electronics, such as the heating device 106 and the flow control device 104 using a similar control signal scheme.

FIG. 4C shows a circuit diagram for a circuit 400C that uses multiple carrier frequencies to provide amplitude control of output. The circuit 400C can be implemented on a printed circuit board of the control circuit 116. The circuit 400C can be used to control the amplitude of output signals provided to interface electronics, such as the heating device 106 and the light source 108. The circuit 400C generally includes band pass filters, an amplitude detector, and an output amplifier. In the example depicted in FIG. 4C, the circuit 400C uses fourth order active filters to create two band pass filters (e.g., 10 kHz filter, 14 kHz filter), although in other examples, the number of band pass filters can be increased based on the number of interface electronics that are controlled by the control circuit 116. The amplitude of each frequency determines the intensity, voltage, or current provided as output to each respective channel. In this respect, by increasing the sharpness of the band pass filters and/or by using frequency notch filters, the amount of cross-talk between channels can be reduced.

Methods of Use

Figure 5:
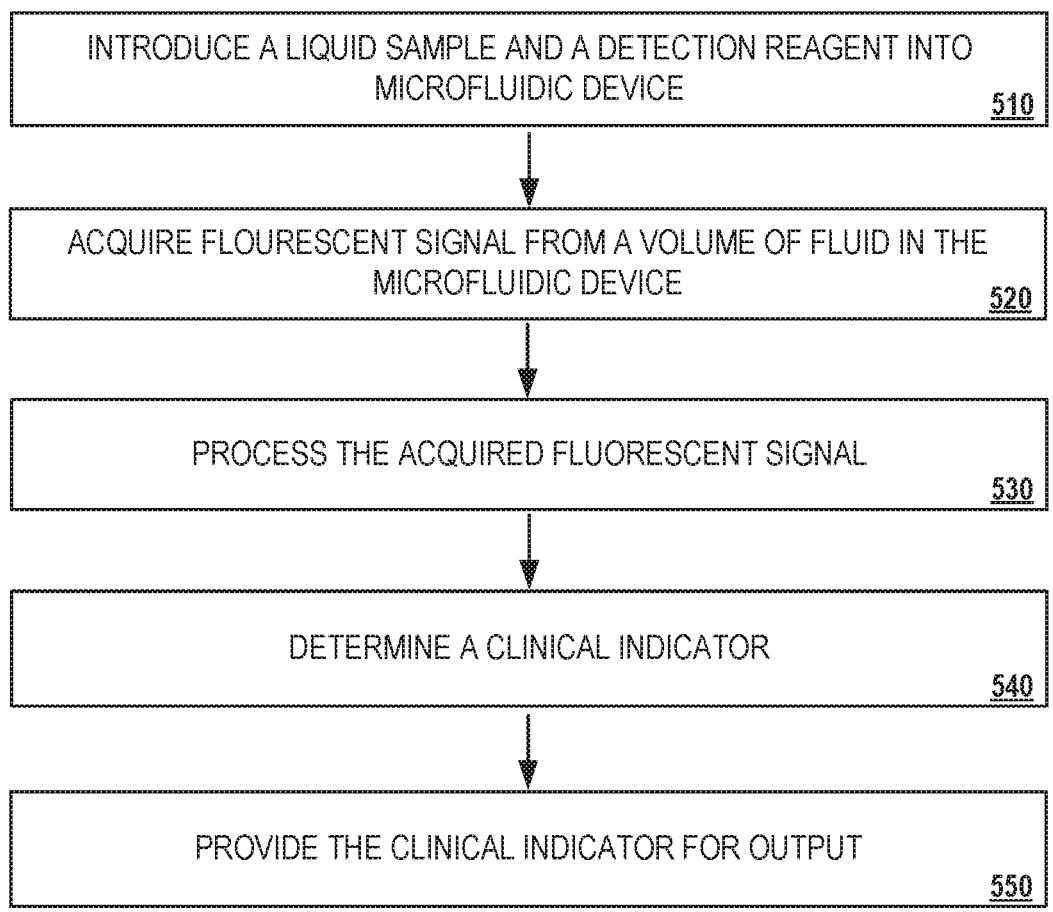
FIG. 5 is a flowchart for an example of a process for performing fluoroscopy using the portable wide field fluorimeter system of FIG. 1A.

FIG. 5 is a flowchart for an example of a process 500 for performing fluoroscopy using the portable wide field fluorimeter systems described herein, e.g., in FIG. 1A. Briefly, the process 500 can include introducing a liquid sample and detection reagent into a microfluidic device (510), acquiring a fluorescence signal from a volume of fluid in the microfluidic device (520), processing the acquired fluorescence signal (530), determining a clinically relevant indicator (540), and providing the clinically relevant indicator for output (550).

In general, the process 500 is described below in reference to the system 100, although any of the systems discussed herein can also be used to perform the operations of the process 500. As examples, the process 500 can be performed using the system 700 depicted in FIGS. 7A-D, or alternatively, using the system 750 depicted in FIGS. 7E-F. In some instances, the process 500 can be performed at the point-of-care, e.g., at a remote field site without a centralized laboratory facility.

In more detail, the process 500 can include the operation of introducing a liquid sample and detection reagent into a microfluidic device (510). For example, an operator can introduce a liquid sample and detection reagent into the microfluidic device 102 with the use of the flow control device 104. As discussed above, the liquid sample and the detection reagent can be mixed prior to introduction into the microfluidic device 102. In other instances, the liquid sample and the detection reagent can be introduced sequentially into the microfluidic device 102.

The process 500 can include the operation of acquiring a fluorescence signal from a volume of fluid in the microfluidic device (520). For example, the fluorescence signal can be acquired by the camera 112, which in some instances, is a camera of a smartphone. As discussed above, the fluorescence signal is acquired based on capturing fluorescence emitted by fluorescing probes within a volume of fluid that is collected in a channel and/or chamber of a fluidic circuit contained in the microfluidic device 102 (e.g., the chamber 252 as depicted in FIG. 2A). The emission light is collected through the optical assembly 110, which includes components to improve light collection efficiency and can be used to, for instance, reduce signal-to-noise ratio in relation to background fluorescence in a captured image.

The process 500 can include the operation of processing the acquired fluorescence signal (530). For example, the analyzer device 114 can process a fluorescence readout in a raw image that is captured by the camera 112. As discussed above, the analyzer device 114 can run image processing and/or detection software that allows the analyzer device 114 to, for example, improve image quality, improve signal-to-noise ratio, or interpret results based on detected fluorescence. In one example, the analyzer device 114 can be configured to use intensity of fluorescence in a captured image to determine if the liquid sample includes an antibiotic resistant bacteria, as shown in FIG. 8A. In another example, the analyzer device 114 can be configured to detect changes in fluorescence over a period of time during which a fluorometric assay is performed using the system 100 to identify AR susceptibility. As discussed above in reference to FIG. 8B, the changes in fluorescence can be used to determine whether an antibiotic can be used to effective treat a known pathogen present in a liquid sample.

The process 500 can include the operation of determining a clinical indicator (540). For example, the analyzer device 114 can determine the clinical indicator based on processing the fluorescence readout of a captured image in step 530. In some instances, the clinical indicator can be a determination as to whether a tested liquid sample includes a pathogen that is resistant to a certain antibiotic. In other instances, the clinically relevant indicator is a level of a bacterial enzyme determined based on the intensity of the fluorescent signal. In some other instances, the clinical indicator can be a diagnosed susceptibility to a certain clinical condition, such as UTI or meningitis.

The process 500 can include the operation of providing the clinically relevant indicator for output (550). For example, the clinical indicator can be provided to an operator that uses the system 100 to perform the assay, e.g., by displaying the results on a display associated with the analyzer device 114 or by generating a printout of the results using an associated printing device. In other instances, results can be transmitted to central data processing facility over a network, such as a wireless local area network (WLAN) or a wide area network (WAN) such as the Internet. The results can include, for instance, a graph of representing the detected changes in fluorescence for a liquid sample over a specified time period, e.g., 60-minutes. Alternatively, the results can include an indication as to whether a patient associated with the liquid sample is identified as being susceptible to AR based on the results of a fluorometric assay. For example, if a change in fluorescence is detected in a liquid sample over the time period during which the fluorometric assay is performed, then the patient can be identified as being susceptible to AR. In some implementations, the operator may be presented with different options, e.g., through a display of the analyzer device 114, to select an option for the amount and type of results to view, print, save, or edit the results.

Figure 6:
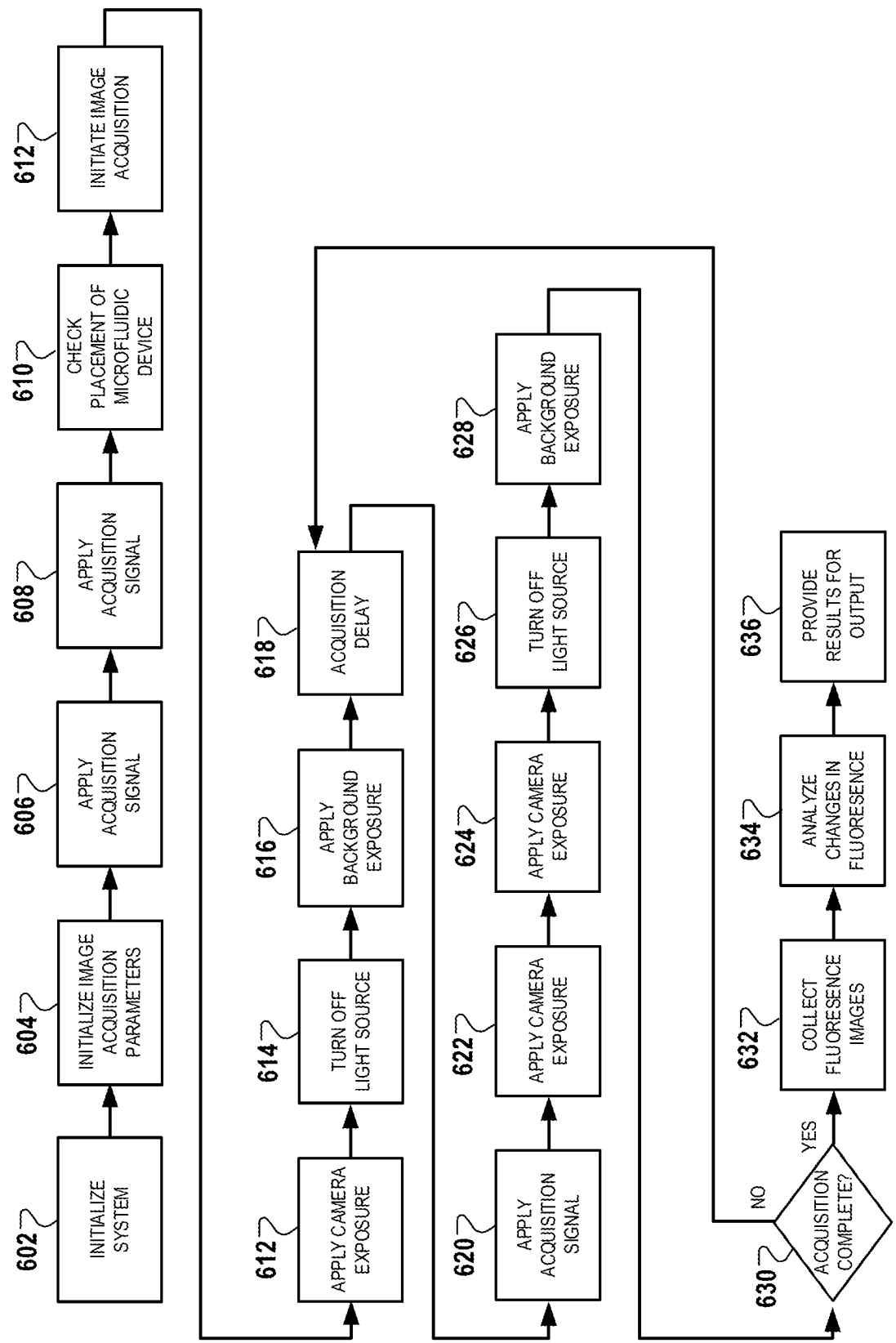
FIG. 6 is a flowchart for an example of a process for processing a fluorescence signal collected by the portable wide field fluorimeter system of FIG. 1A.

FIG. 6 is a flowchart for an example of a process 600 for processing a fluorescence signal collected by the system 100 of FIG. 1A. The operations of the process 600 can generally be categorized into three stages: (1) initialization, (2) acquisition, and (3) analysis. During the initialization stage, excitation light is applied to a volume of a sample fluid in a microfluidic device for fluorescence detection. During the acquisition stage, light emitted by the volume of fluid in the microfluidic device is acquired by a camera. During the analysis stage, image data collected in the acquisition stage is processed to generate a fluorescence readout for the liquid sample.

In more detail, during the initialization stage, the system 100 is initialized for headphone output (602). For example, software that runs on the analyzer device 114 can be initialized to provide a control signal for output to interface electronics through the control circuit 116. Camera parameters for image acquisition are then initialized (604). For example, software that runs on the analyzer device 114 can imaging parameters, such as the time interval for collecting images (e.g., 60 minutes), a frequency of image collection (e.g., every one to fifteen minutes), or parameters associated with image capture (e.g., exposure, desired signal-to-noise ratio, white level, etc.). A sinusoid signal (e.g., a 10 kHz sinusoid signal) is then generated to enable the light source 108 to generate an excitation light to illuminate a fluid (e.g., a liquid sample and a detection reagent) within the microfluidic device 102 (606, 608, 610).

The placement of the microfluidic device 102 is then checked (612). For example, software running on the analyzer device 114 can confirm whether the microfluidic device 102 has been properly placed on top of a holding device that receives the microfluidic device 102. The holding device (not shown in FIG. 1A) can include optical sensors that identify the correct placement of the microfluidic device 102 based on, for example, checking for certain features representing a specified region of the microfluidic device 102. Alternatively, placement of the microfluidic device 102 can also be manually checked by an operator (e.g., a healthcare provider). The operator can then begin image acquisition (614). For example, the operator can press a button on the exterior of the system 100 that provides a control signal to the camera 112 to initiate image acquisition.

During the acquisition stage, an exposure level is initially configured for the camera 112 (614). For example, in one implementation, an exposure level is set such that the camera 112 collects an emitted fluorescence signal for seven seconds. The light source 108 is then turned off so that excitation light is no longer supplied to a volume of fluid contained in the microfluidic device 102 (616). The exposure level is then configured again for the camera 112 (618). A thirty second wait is applied after the camera 112 completes image acquisition in the prior step (620). A sinusoid signal (e.g., a 10 kHz sinusoid signal) is then generated to enable the light source 108 to generate an excitation light to illuminate a fluid (e.g., a sample fluid containing a detection reagent) within the microfluidic device 102 (622). The exposure level is then configured again for the camera 112 (624). The light source 108 is then turned off so that excitation light is no longer supplied to the volume of sample fluid contained in the microfluidic device 102 (626). The exposure level is then configured again for the camera 112 (628). At step 630, the system determines if image acquisition has been completed. If the system 100 determines that image acquisition is not complete, then the process 600 reverts back to step 620 to collect additional image data. For example, the operator 102 can manually select an option to collect additional images, or alternatively, the analyzer device 114 can automatically re-initiate the image acquisition process. In the second example, the decision to re-initiate the image acquisition can be based on initially processing image data collected at steps 620-628 and determining that the collected images have capture errors and/or low quality images.

In some implementations, during image acquisition, the system 100 is configured to increase frame rate of image collection every three to thirty seconds to reduce camera noise effects. For example, images collected can be at step 628 at a faster frame rate compared to images collected at step 624, which then is collected at a faster frame rate compared to images collected at step 618.

If the system 100 determines at step 630 that the image acquisition is complete, then the analysis stage is initiated. Data representing fluorescence emission from the volume of fluid within the microfluidic device 102 is extracted from the captured images (632). For example, as discussed in more detail below, the analyzer device 114 can obtain a fluorescence readout in which pixel values represent intensities of fluorescence emission from a volume of liquid in the microfluidic device 102. The fluorescence emission data extracted from a captured image is analyzed by the analyzer device 114 (634). For example, multiple images can be captured over a period of time (e.g., 60 minutes) to determine the change in emitted fluorescence after a detection reagent has reacted with a liquid sample introduced into the microfluidic device 102.

As discussed above, the observed fluorescence change can be used to determine the presence of a target analyte and/or target pathogen in the liquid sample. For example, if the target pathogen is an antibiotic resistant pathogen, then the liquid sample can include a sample extracted from the liquid, the antibiotic of interest, and the detection reagent can include a probe that is rendered fluorescent when activated by a specific target analyte, such as an enzyme expressed by a specific target pathogen. If the antibiotic resistant bacteria are present in the patient sample, then a reaction between the fluorescent probe and the antibiotic resistant bacteria should cause the emission of fluorescent signal. In this example, a lower intensity of fluorescence detected in the readout can be used to identify the presence of non-resistant bacteria whereas a higher intensity of fluorescence detected in the readout can be used to identify the presence of antibiotic resistant bacteria. The results of the fluorescence analysis in step 634 are then provided for output (636). The detection results can be provided for output to the operator on a display of the analyzer device 114, transmitted to for storage in an external computing device that is connected via USB to the analyzer device 114, or transmitted over a network (e.g., a cellular-based network, or a wireless local area network) to a central data processing server.

Exemplary Implementations

Figure 7A:
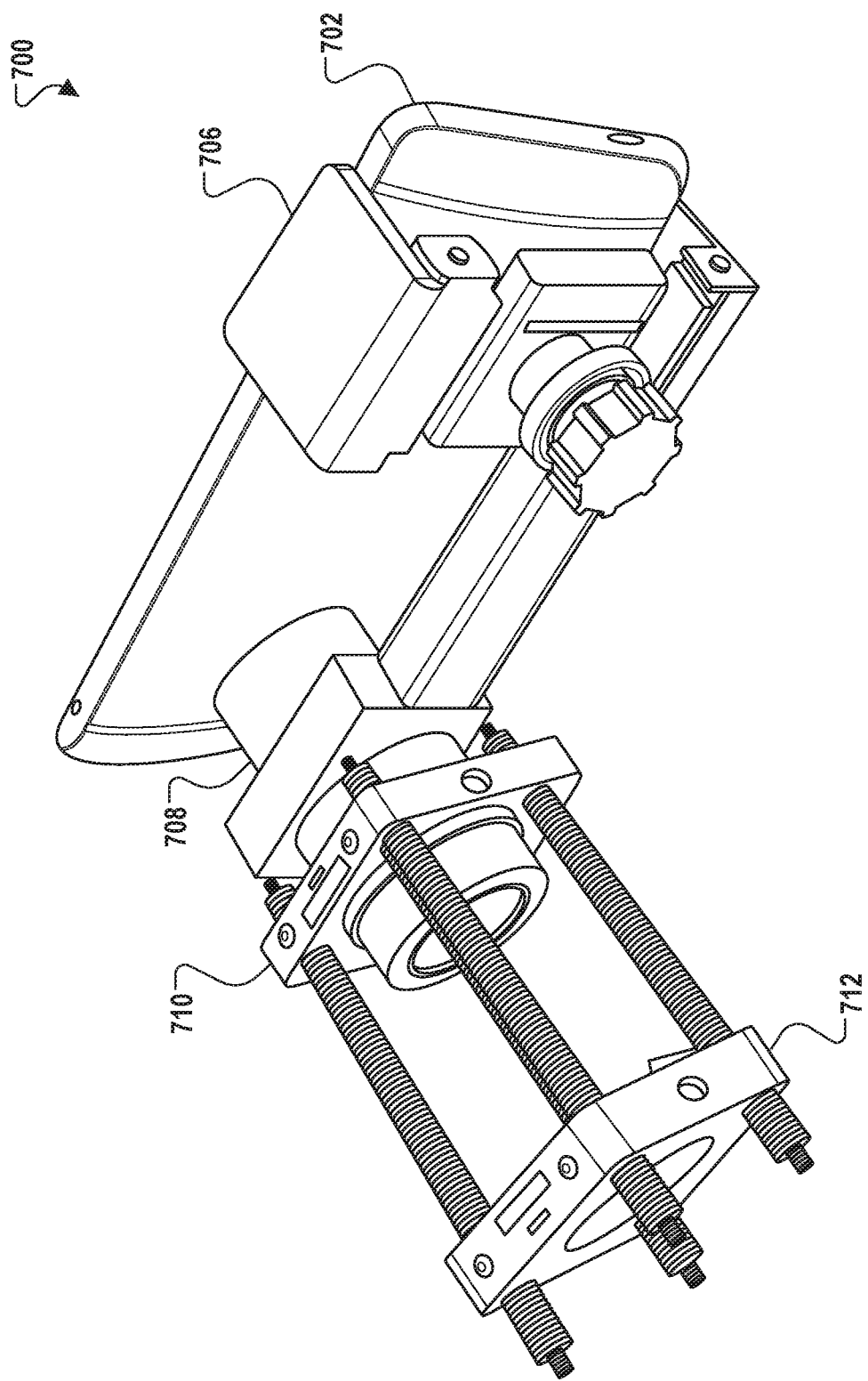
Figure 7B:
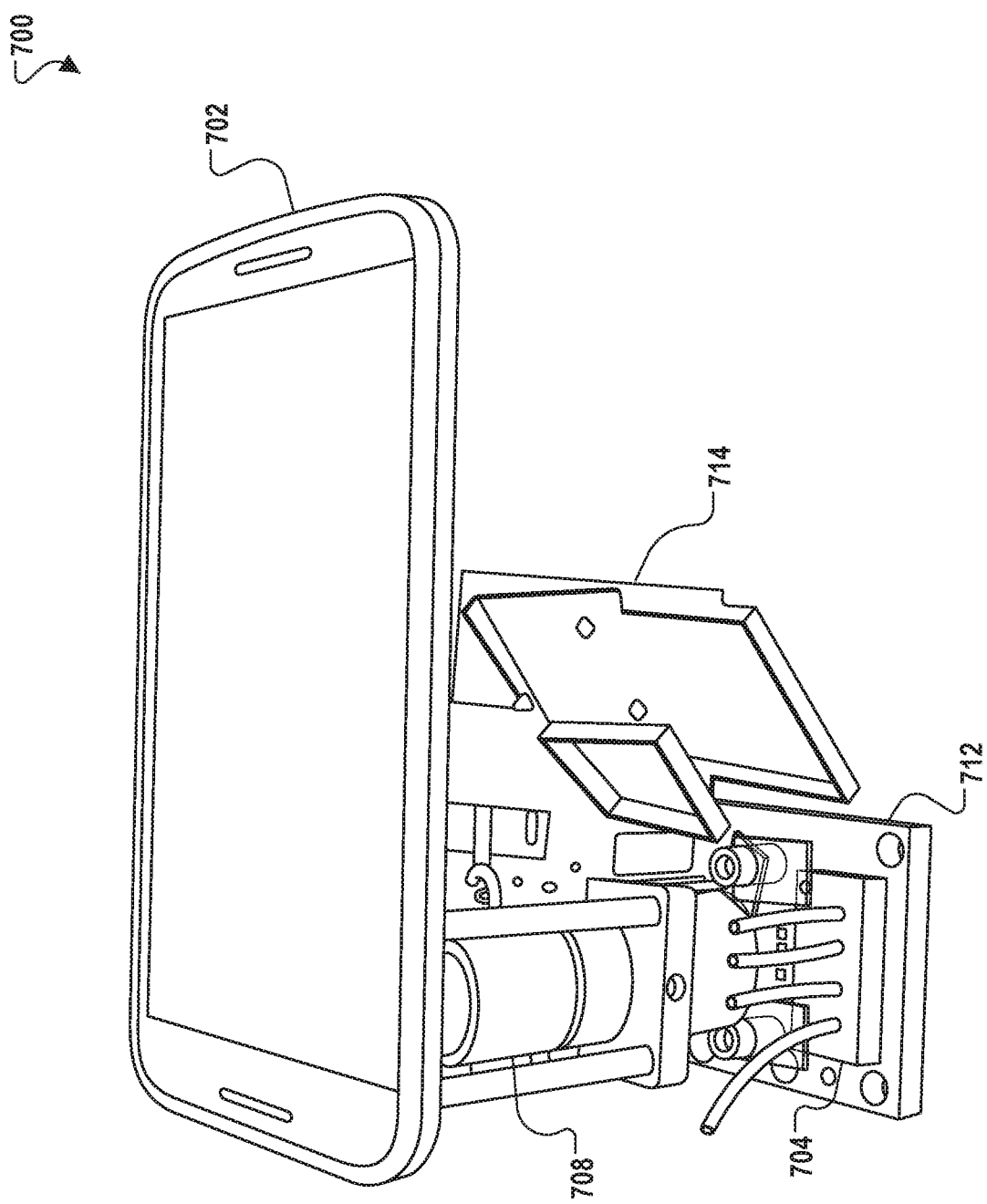
Figure 7E:
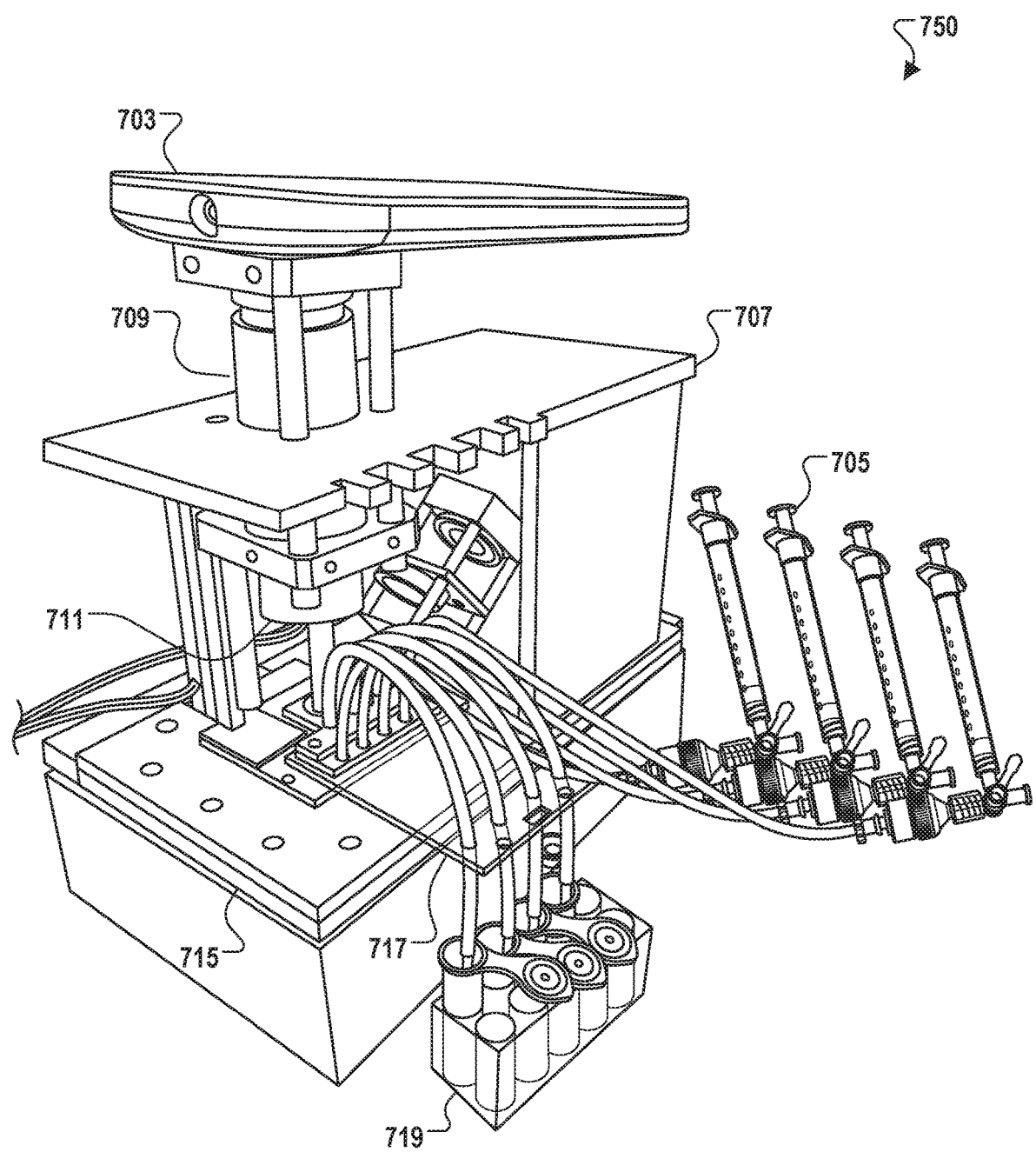
FIGS. 7E-F are schematic diagrams that illustrate an example of another implementation of the portable wide field fluorimeter system described herein.

FIGS. 7A-D are schematic diagrams that illustrate an example of one specific implementation of the system 100 of FIG. 1A. FIGS. 7A and 7B illustrate perspective views of a system 700, while FIGS. 7C and 7D illustrate a front and a side view of the system 700, respectively. The system 700 includes a smartphone 702 that runs image collection and/or image processing software and can be used as an analyzer device for collecting, processing, and analyzed image data representing a fluorescence signal emitted based on a reaction of a liquid sample and a detection reagent within a microfluidic device 704 (not shown in FIG. 7A).

Although not depicted in FIGS. 7A-D, the components of the system 700 can be contained in a housing that prevents ambient light from entering the optical assembly 708 during image acquisition. For example, the housing can be made from a durable yet lightweight material that contains all of the imaging components of the system 700. The housing can include gripping elements and/or mounting portions for securing components for easy access and removal during an imaging operation.

Referring to FIGS. 7A-D, image data is collected, in this implementation, by an integrated camera of the smartphone 702 (e.g., a back-facing camera). The smartphone 702 is secured in place by a holder 706, which in the example depicted in FIG. 7A, includes a clamp with an adjustable width for securing mobile devices of different dimensions on top of the holder 706. Once positioned on top of the holder 706, the smartphone 702 can be secured in place so that its camera can be aligned to with lenses of an optical assembly 708 to allow for image collection. As discussed above, the alignment of the components of the optical assembly (e.g., tube lens, objective lens, emission filter, and polarizer) creates an emission optical path that allows the camera of the smartphone 702 to collect an image with greater signal-to-noise ratio relative to an image collected using the camera of the smartphone 702 without the optical assembly 708. This is because the optical assembly 708 can be used to increase the numerical aperture compared to the numerical aperture of the camera lens of the smartphone 702 alone (thereby increasing light collection efficiency). In the example depicted in FIGS. 7A-D, the holder 706 is also secured by a cage system 710. The cage system 710 includes four pillars that extend from a plane of the clasp of the holder 706 to a plane of a base plate 712 on which the microfluidic device 704 is placed.

The system 700 includes a light source 716 (shown in FIG. 7D) that provides excitation light for fluorescence imaging by the camera of the smartphone 702. The light source 716 is secured in place by a holder 714 (shown in FIG. 7B), which allows the light source 716 to be arranged at a certain angle (e.g., 45 degrees) relative to the top surface of the microfluidic device 720 to reduce optical contamination in the emission optical path of the optical assembly 708. The light source 716 can include one or more LEDs that provide light at a specified excitation wavelength. For example, the light source 716 can be 470 nm LED light source. Although not depicted in FIGS. 7A-D, in some implementations, the system 700 can also include a beam dump as discussed above in reference to FIG. 3.

The system 700 also includes a control board 718 that includes one or more circuits for controlling interface electronics of the system 700. The control board 718 can be connected to the smartphone 702 through its headphone jack and can be configured to receive analog signals that are then provided to interface electronics, e.g., the light source 716, a heating device (not shown in FIGS. 7A-D), an associated flow control system (also not shown in FIGS. 7A-D), among other components discussed above. For example, as discussed above in FIGS. 4A-C, the control board 718 can include circuits that are connected to the smartphone 702 through its headphone jack and receive analog control signals that adjust the operation of the interface electronics. As one example, the control board 718 can transmit control signals to the light source 716 adjust the intensity of the excitation light provided by the light source 108 to illuminate a volume of fluid within the microfluidic device 102 that is imaged. As another example, the control board 718 can control the amount of heat supplied to the microfluidic device 712 when performing a fluorometric assay.

Figure 7F:
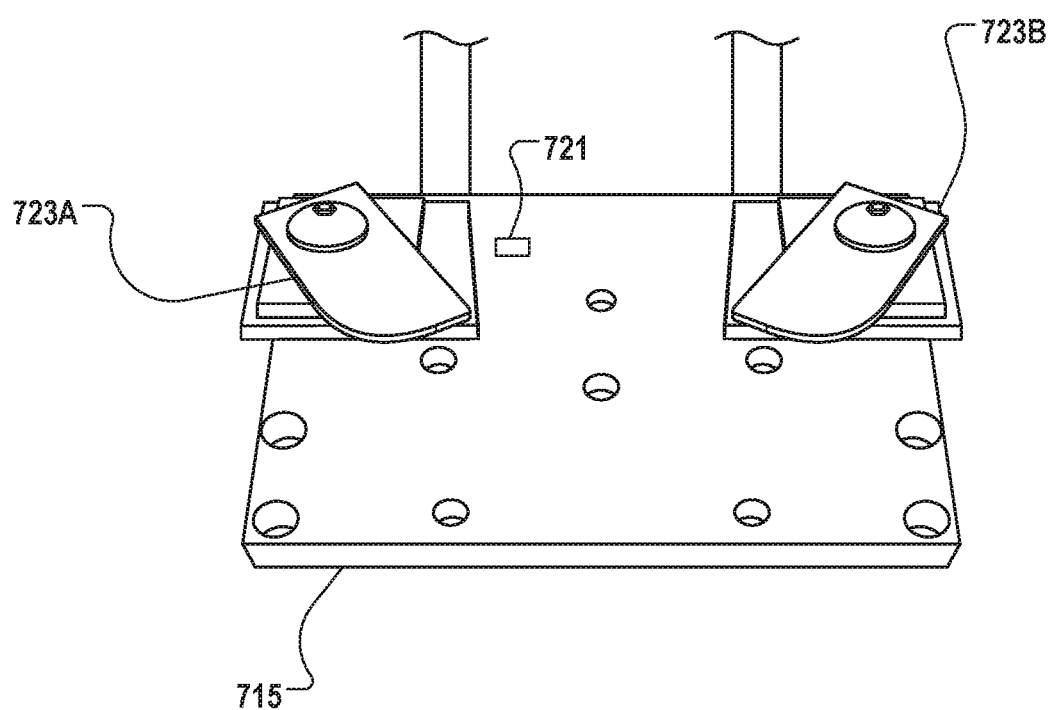

FIGS. 7E-F are schematic diagrams that illustrate an example of another specific implementation of the system 100 of FIG. 1A. FIG. 7E illustrates a perspective view of a system 750, while FIG. 7E illustrates a top view of a heating plate 715 that is used in conjunction with the system 750 for heating a volume of fluid that is introduced into a microfluidic device 717. The system 750 includes a smartphone 703 that runs image collection and/or image processing software. For example, the smartphone 704 can be used as an analyzer device for collecting, processing, and analyzed image data representing a fluorescence signal emitted based on a reaction of a liquid sample and a detection reagent within the microfluidic device 717.

Components of the system 750, e.g., interface electronics, wires, etc., can be contained in a housing 707. Although not depicted in FIG. 7E, in some implementations, the system 750 can be contained in an external housing that prevents ambient light from entering an optical assembly 709 during image acquisition. For example, the housing can be made from a durable yet lightweight material that contains all of the imaging components of the system 700. The housing can include gripping elements and/or mounting portions for securing components for easy access and removal during an imaging operation.

The system 750 also includes an optical assembly 709 that is secured, mounted, or otherwise attached to the smartphone 703 to create an optical emission path fluorescence detection as in a similar manner as discussed above for the system 700. The system 750 additionally includes a light source 711 that provides an excitation light for fluorescence excitation in a volume of liquid that is introduced into the microfluidic device 203.

As shown in FIG. 7E, fluid (e.g., a liquid sample, detection agent, etc.) is introduced into the microfluidic device 717 using a flow control device 705, which, in this example, is a syringe vacuum that applies a negative pressure to draw a volume of fluid into the microfluidic device 717 from the sample containers 719. In other implementations, other suitable flow control devices can be used, as discussed above. The microfluidic device 717 is placed on top of a heating pad 715, which is used to maintain a specified temperature necessary for optimal enzymatic action for a performing particular fluorometric assay. The heating pad 715 is placed on top of a sample holder, which can be elevated relative to the sample containers 719 (as shown in FIG. 7E) to reduce the length of tubing needed to extract fluid from sample containers 719.

The tubing can include FEP-lined tubing to protect against leaching of compounds out of a fluid sample containing reagents or other liquids prior to fluid introduction into the microfluidic device 203. For further protection, the microfluidic device 203 can constructed from polymethylmethacrylate (PMMA), which is inert and can be used to prevent against interference with biological reactions even if some leaching does occur. To prevent the tubing from touching the sample fluid, pure FEP tubing (or stainless steel tubing) can be inserted into FEP-lined tubing and inserted into the sample containers 719.

As discussed above, a flow control device 705 that is a syringe vacuum is used to draw fluid from the sample containers 719 and into the fluidic circuit of the microfluidic device 203. Once an appropriate amount of fluid (e.g., 50 microns) is withdrawn, a 3-way stopcock can be first used to equalize the pressure of the syringe vacuum to atmospheric pressure prior to sealing exit tubing to prevent unwanted fluid motion. In the example depicted in FIG. 7E, a single syringe is used for each fluidic circuit (e.g., four fluidic circuits), which allows sequential insertions of sample while data monitoring is performed. In other examples, a single syringe vacuum can be connected to each of the four fluidic circuits to withdraw sample fluid into each of the four fluidic circuits using a single syringe vacuum.

In some implementations, a filter in the outlet can be used to set the volume of fluid to introduce into the microfluidic device 717. In such implementations, when the filter is wet, flow is severely impeded, which effectively stops fluid insertion. For example, a combination of small pore hydrophilic filter and a hydrophobic filter can be used to completely eliminate fluid motion in either direction once wetted. Related to the prior point, since the pathogen are trapped on the filter, the assay can be repeated by flushing more beta-leaf through the filter.

FIG. 7F is a schematic diagram that illustrates an example of the heating pad 715. As discussed above, in some instances, the microfluidic device 203 is placed on top of the heating device so that heat can be supplied to a volume of fluid that is introduced into the microfluidic device 203 to maintain a designated temperature associated with the particular fluorometric assay to be performed using the system 750. The heating pad 715 includes a membrane temperature sensor 721 that is used to accurately estimate a temperature of the microfluidic device 203. The sensor 721 can be separated from the heating plate 715 (e.g., by two layers of 1/16" acrylic material) to ensure that temperature readings collected by the sensor 731 accurately represent the membrane temperature. Temperature data collected by the temperature sensor 71 can be used to provide feedback signals that control the power output to the heating pad 715. For example, the feedback signals can be used to maintain a membrane temperature that is accurate within one degree Celsius. The heating pad 710 additionally includes two spring claims 723A and 723B that are used to secure the microfluidic device 203 in place when positioning the microfluidic device 203 for imaging.

Clinical Applications

In some implementations, the portable wide field fluorometric system described herein can be used to provide ESBL characterization for point-of-care testing. In such implementations, the system can be adapted to allow for testing in multiple testing conditions, provide temperature control, provide automated mobile device-based image analysis, and enable biological validation on laboratory isolates.

For example, the system can be used to detect β-lactamase by performing a single assay in two channels of microfluidic device. A first liquid sample that includes a target pathogen and associated target analyte, and a β-LEAF probe can be introduced into the first channel. A second liquid control sample that includes only the β-LEAF probe (and not the target analyte) is introduced into the second channel. In this example, the type of β-lactamase (e.g., ESBL or carbapenemase) should be distinguished, because this can be important for treatment. For instance, ESBL often have many sub-categories, such as TEM/SHV mutants or CTX-M types. TEM/SHV mutants tend to display resistance to cefotaxime (a third-generation cephalosporin) but susceptibility to ceftazidime (cephamycin). In contrast, the CTX-M enzymes are often preferentially active against cefotaxime and less active against ceftazidime. The carbapenemases (e.g. KPC, NDM, VIM) cleave imipenem and provide an additional test. Thus, four types of samples can be tested using the system:

(1) bacterial solution, β-LEAF probe, cefotaxime antibiotic solution;

(2) bacterial solution, β-LEAF probe, ceftazidime antibiotic solution;

(3) bacterial solution, β-LEAF probe, imipenem antibiotic solution; or (4) bacterial solution, β-LEAF probe (no antibiotic solution).

To test each sample in parallel, the microfluidic device can have four independent channels that each receive one of the samples (as depicted with the microfluidic device 102, 202 in FIGS. 2A-K).

When applied in a point-of-care setting, the system can be configured to provide optimum enzymatic activity when performing a fluorometric assay. For example, a heating device can be embedded in the sample holder on which a microfluidic device is placed to provide heat to a volume of fluid that is introduced into the microfluidic device. This ensures that the temperature of sample is maintained at 37° C. (e.g., optimal temperature for enzymatic activity). A thermistor can be used to ensure an accurate sample temperature. Temperature control can be maintained using a Proportional-Integral-Derivative (PID) algorithm and interfaced to the thermistor and heating device via the communication interface such as a headphone jack of a mobile device used for imaging. As discussed throughout, this interface can also be used to control LED excitation and synchronize excitation with camera acquisition (to avoid photo-bleaching). Additionally, the emission optical path within an optical assembly can be sealed to prevent accidental alteration at the point-of-care while providing protection to the microfluidic device during image acquisition and analysis. In some instances, a sample holder can include alignment pins to allow reproducible placement of microfluidic devices. Power can be provided to the system using a standard AC/DC converter.

In some instances, data collected by the system in the point-of-care can be validated using assays that are performed in a research laboratory setting with using commercially available bacterial strains from American Type Culture Collection (ATCC), such as *Klebsiella pneumonia*: 700603(ESBL SHV-18, quality control strain), 13883 (lactamase-, quality control strain); *Escherichia coli*: BAA-2355 (ESBL CTX-M9), 25922 (lactamase-, quality control strain); *Enterobacter cloacae*: BAA-2468 (carbapenemase NDM-1), 13047 (lactamase-); and *Haemophilus influenza*: 43335 (β-lactamase ROB-1), 10211 (lactamase-, quality control strain). To perform validation testing, these bacterial strains can be introduced into a human sample such as urine or CSF. To simulate moderate pleocytosis or pyuria, neutrophils acquired from whole human blood can be added (1e5 cells/ml) and confirmed using flow cytometry. The number of cells can be filtered out through a 13 mm diameter, 5 µm pore filter, while still maintaining high flow rates.

Additionally, in some implementations, the system can be calibrated to allow for the preliminary diagnosis of UTI and meningitis in a human sample based on ESBL detection. In such implementations, the calibration can be performed based on preliminary ESBL detection data that is collected in a laboratory environment. For example, for calibration for UTI diagnosis, 25 ESBL resistant isolates can be studied using a binomial power calculation for 80% sensitivity at 95% confidence. To ensure these numbers are achieved, 1 ml of a urine sample is be stored at 4° C. while the remainder is subject to standard culture-based analysis (e.g. gram stain, MIC and ESBL detection). From these stored specimens, 25 penicillinase-producing specimens, 25 cephalosporinase-producing specimens (which destroy many cephalosporins, but are ineffective against 3' generation cephalosporins), 25 ESBL-producing specimens, and 25 non-producing specimens are tested with the platform for children less than 1 year of age and for patients greater than 1 year of age. Urine is collected with mid-stream catch or catheter. For young children unable to control urination, bagged urine specimens that have been changed repeated and are at minimal risk of contamination are used (catheterized samples, which provide better quality samples are not commonly obtained for infants unless severely ill, in contrast to high-income countries). However, techniques can focus on conditions that are commonly encountered in LMICs. ESBL quality control strains can be used to ensure consistent performance.

As another example, for calibration for meningitis diagnosis, similar techniques can be used as discussed above with respect to calibration for UTI diagnosis. However, due to the low numbers of meningitis cases, 25 β-lactamase producers, and 25 non-producers (with no age criteria) can be studied. Although the low numbers are not ideal, there is often broad overlap in the pathogens that cause UTI and meningitis, which allows ΔFs cutoffs from the UTI to suffice in meningitis.

In some instances, field testing of the system and techniques discussed herein can be performed to validate performance of the portable wide field fluorimeter system. For example, performance of the system can be validated based on unprocessed patient samples using regionally-produced microfluidic devices (e.g., microfluidic devices that are locally produced in a LIMC).

UTI detection performance by the portable wide field fluorimeter system can be validated as one example. In this example, urine from a patient can be collected using similar collection techniques described above. Microscopic analysis and rapid gram staining can be used to select specimens with high probability of bacterial UTI. These results can often be obtained within 2 hours. One hundred specimens of suspected bacterial UTI can then be collected from patients less than 1-year old and patients older than 1-year old (with a total of 200 patients). The selected specimens can undergo standard microbiological testing and testing using the portable wide field fluorimeter system in parallel. In addition, 100 control specimens for each age group can also be collected. The sensitivity/specificity of the system can be calculated based on comparing microbiological testing and testing using the system (with a sufficient sample size to test for 80% sensitivity with 95% confidence for each group) and used to estimate the effect of adoption of POC testing using the system on initial effective treatment rates.

Meningitis detection performance by the portable wide field fluorimeter system can be validated as a second example. In this example, CSF from a patient can be collected using similar collection techniques described above. Rapid gram stain and microscopic analysis can be used to identify 25 patients at high risk for bacterial meningitis for patients aged less than 1-year old and patients older than 1-year old. These results can often be obtained in less than 2 hours. These specimens can undergo standard microscopic analysis and testing using the system in parallel as discussed above for validation of UTI detection performance. Twenty-five patients at low risk for bacterial meningitis for both age groups can also be studied.

EXAMPLES

Experiments were conducted to test the fluorometric assay techniques discussed throughout this document.

Example 1—Fluorometric Assay in a 96-Well Plate

In one experiment, fluorometric assay techniques were examined in a 96-well plate. In this experiment, the detection reagent was a 20 µM β-LEAF Bodipy-FL probe solution (2×stock) that was prepared in 40% DMSO in PBS, and an antibiotic solution was a 100 mM/ml cefazolin solution (4×stock) that was prepared by dissolving the antibiotic powder in PBS. Assays were performed in 96-well, white, clear-bottom plates in a total volume of 100 µl. Two different types of liquid samples were prepared. A first liquid sample (which included the antibiotic solution) was prepared by combining the 25 µl bacterial suspension, 50 µl of probe 2×stock solution, and 25 µl antibiotic 4×stock solution. A second liquid sample (which did not include the antibiotic solution) was prepared by a 25 µl bacterial suspension, 50 µl of the 10 µM β-LEAF probe, and a 25 µl of a PBS solution. The resultant buffer concentrations were 20% DMSO in PBS for each liquid sample.

Time course assays were carried out with each of the two liquid samples by monitoring β-LEAF cleavage by measuring fluorescence for 60 minutes, at 1 minute intervals using a Spectramax® M5 Plate Reader (Molecular Devices). Instrument settings were kept as excitation at 450 nm and emission at 510 nm. The temperature was maintained at 37° C. throughout. Fluorescence was measured in a machine specific standard unit.

Example 2—Fluorometric Assay Performed Using a Portable Wide Field Fluorimeter In another experiment, fluorometric assay techniques were examined using a microfluidic device (e.g., the microfluidic device 102) and fluorescence images were collected using a portable wide field fluorimeter similar to the system 700 depicted in FIGS. 7A-D. In this experiment, the detection reagent was a 20 μM β-LEAF Bodipy-FL probe solution (2×stock) that was prepared in 40% DMSO in PBS, and an antibiotic solution was a 100 mM/ml penicillin G solution (4×stock) that was prepared by dissolving the antibiotic powder in PBS. Two different types of liquid samples were prepared. A first liquid sample (which included the antibiotic solution) was prepared by combining the 25 μl bacterial suspension, 50 μl of probe 2×stock solution, and 25 μl antibiotic 4×stock solution. A second liquid sample (which did not include the antibiotic solution) was prepared by a 25 μl bacterial suspension, 50 μl of the 10 μM β-LEAF probe, and a 25 μl of a PBS solution. The resultant buffer concentrations were 20% DMSO in PBS for each liquid sample.

The liquid samples were mixed prior to introduction into the microfluidic device, and were introduced using a vacuum provided by syringes. After fluid introduction, a 3-way valve next to the syringe released the vacuum before sealing a tubing. The microfluidic device was then placed underneath an optical assembly attached to a camera of a mobile device for imaging.

Data acquisition involved collecting a fluorescent reading by the camera every 3 seconds. The images were acquired in RAW format (to avoid spectral infidelity that occurs with JPEG formats). Fluorescence was measured in a machine specific standard unit. Illumination was provided by a 447.5 nm high power LED followed by 450 nm Band pass filter (FWHM 10 nm). Illumination was kept on for the entire measurement. In some instances, the technique was not used for longer time-course measurements to prevent to photobleaching. In such instances, the light was turned on every 30 seconds using the smartphone interface circuit for the image capture.

The liquid samples introduced into the microfluidic device were maintained at 37° C. throughout the imaging procedure. The temperature was maintained using a 10-ohm power resister clamped below the sample stage, a 7.5 V power supply, a solid-state relay and a proportional-integral device (PID) control. Temperature feedback was provided by a miniature Pt100 resistance temperature detector mounted in the clamping assembly next to the microfluidic device.

To analyze image data, a region of interest was selected over an area of bacteria capture corresponding to a chamber of the microfluidic device was the liquid samples were collected. Fluorescence data was extracted in a green channel. Another region of interested was selected in the same channel, but in an area where bacteria were not trapped. This measurement was used for background subtraction.

In this example, the microfluidic device was assembled using $\frac{1}{16}$" PMMA, which was fabricated using a 100 W $CO_2$ laser. A 200 nm pore size $Al_2O_3$ filter (GE Anopore) was made opaque using electroless nickel deposition as follows. The filter was soaked for 30 seconds in 5 ml of acetone and 50 microliters of 5 mg/ml solution of palladium (II) chloride ($PdCl_2$) in DMSO ($C_2H_6OS$). Filters were air dried and then submerged for 5 minutes in an aqueous bath containing 25 g/l nickel (II) sulfate hexahydrate ($NiSO_4.6H_2O$), 15 g/l sodium acetate ($NaO_2C_2H_3$), 4 g/l dimethylamine borane complex ($C_2H_{10}BN$) and 2 mg/l lead (II) acetate trihydrate ($Pb(C_2H_3O_2)_2.3H_2O$), adjusted to pH of 5.9 with sulfuric acid. The final assembly was pressed at roughly 700 PSI using an arbor press for 3 seconds.

Results confirmed the ability of the fluorimeter systems, as discussed herein, to detect the presence of beta-lactamase within a microfluidic device with sufficient signal to noise to allow direct detection of pathogens in urine and CSF.

Example 3—Fluorescence Image Collected by the Portable Wide Field Fluorimeter In another experiment, a fluorescence image of a liquid sample introduced into a microfluidic device was collected and processed by a smartphone camera attached to an optical assembly. FIG. 8A is a representation of a photo of the fluorescent image that was collected by the smartphone camera. The photo depicts fluorescence detected in four chambers of a microfluidic device. In this experiment, the microfluidic device included four channels that each received a different liquid sample. The left-most channel received a liquid sample that included non-resistant bacteria and a fluorescent probe specific to the bacteria. The left-middle channel received a liquid sample that included antibiotic resistant bacteria and a fluorescent probe specific to the bacteria. The right-middle channel received a control liquid sample that included antibiotic resistant bacteria but did not include a fluorescent probe. The right-most channel received another control liquid sample that included a fluorescent probe only but did not include any bacteria.

The results of experiments confirmed that the fluorometric assay techniques discussed within this document can be used to determine an antibiotic susceptibility based on detecting the presence of an antibiotic resistant bacteria in a liquid sample. For example, a higher intensity fluorescence signal was detected in the left-middle chamber compared to the left-most chamber because the bacteria in the liquid sample collected in the left-middle chamber includes antibiotic resistant bacteria. Additionally, no fluorescence was detected in the right-middle and right-most chambers because the liquid sample collected in the right-middle channel did not include a fluorescent probe and the liquid sample in the right-most channel only included a fluorescent probe in its uncleaved form.

Example 4—Fluorescence Signal Changes Over Time Based on Bacterial Samples

Figure 8B:
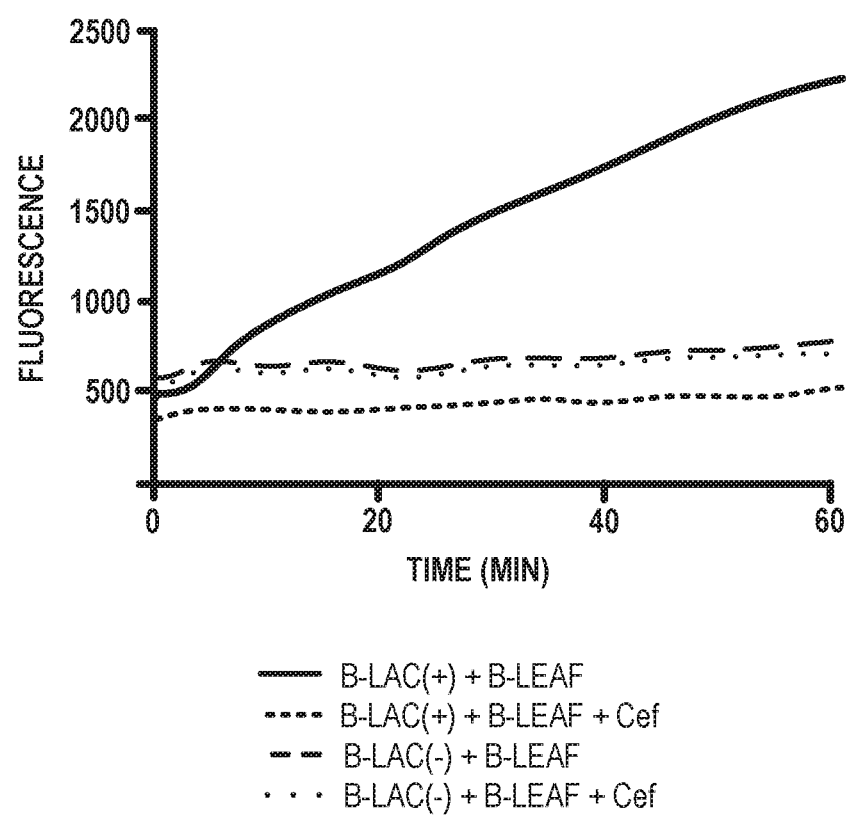
FIG. 8B is a graph that shows results of an experiment in which time course changes in fluorescence were observed during four β-LEAF assays.

In another experiment, changes to detected fluorescence was observed for four different β-LEAF assays over a 60-minute time period. FIG. 8B is a chart that shows the changes to fluorescence for the four different β-LEAF assays. In this example, β-LEAF assays were performed with the two ATCC *S. aureus* control bacterial strains, a known β-lactamase producing strain (B-lac(+)) and a known β-lactamase non-producing strain (B-lac(−)). The bacteria were incubated with a solution that included a fluorescent probe alone, and a solution that included the fluorescent probe and cefazolin (Cef) as a test antibiotic. Four test solutions were prepared and examined for time-course fluorescence intensity changes:

(a) B-lac(+), β-LEAF (β-lactamase producing bacteria; no antibody added)

(b) B-lac(+), β-LEAF, Cef (β-lactamase producing bacteria; antibody added)

(c) B-lac(−), β-LEAF (β-lactamase non-producing bacteria; no antibody)

(d) B-lac(−), β-LEAF, Cef (β-lactamase non producing bacteria; antibody added)

Time-course fluorescence measurements were made for each sample over a 60-minute time period at 1-minute intervals. Results showed that fluorescence intensity for sample A increased over the 60-minute time period, while fluorescence intensity for each of the samples generally did not increase over the 60-minute time period.

As discussed above with respect to FIGS. 1C-D, the time-course fluorescence measurements can be used to determine a suppression of fluorescence change (ΔFs), which is defined as $(\Delta F_{BL} - \Delta F_{BL+antibiotic})/\Delta F_{BL}$, where $\Delta F_{BL}$ and $\Delta F_{BL+antibiotic}$ are the fluorescence rate of change of the β-lactamase only and β-lactamase+antibiotic conditions, respectively. A ΔFs approaching the value of 1 indicates an ineffective antibiotic. For example, in the chart depicted in FIG. 8B, cefazolin (a β-lactam antibiotic) inhibits the cleavage of β-LEAF, which indicates that cefazolin cleavage by β-lactamase with ΔFs very close to the value of 1. Thus, these results indicate that cefazolin would be a poor treatment choice for this pathogen.

Example 5—Antibiotic Susceptibility Testing

Figure 8C:
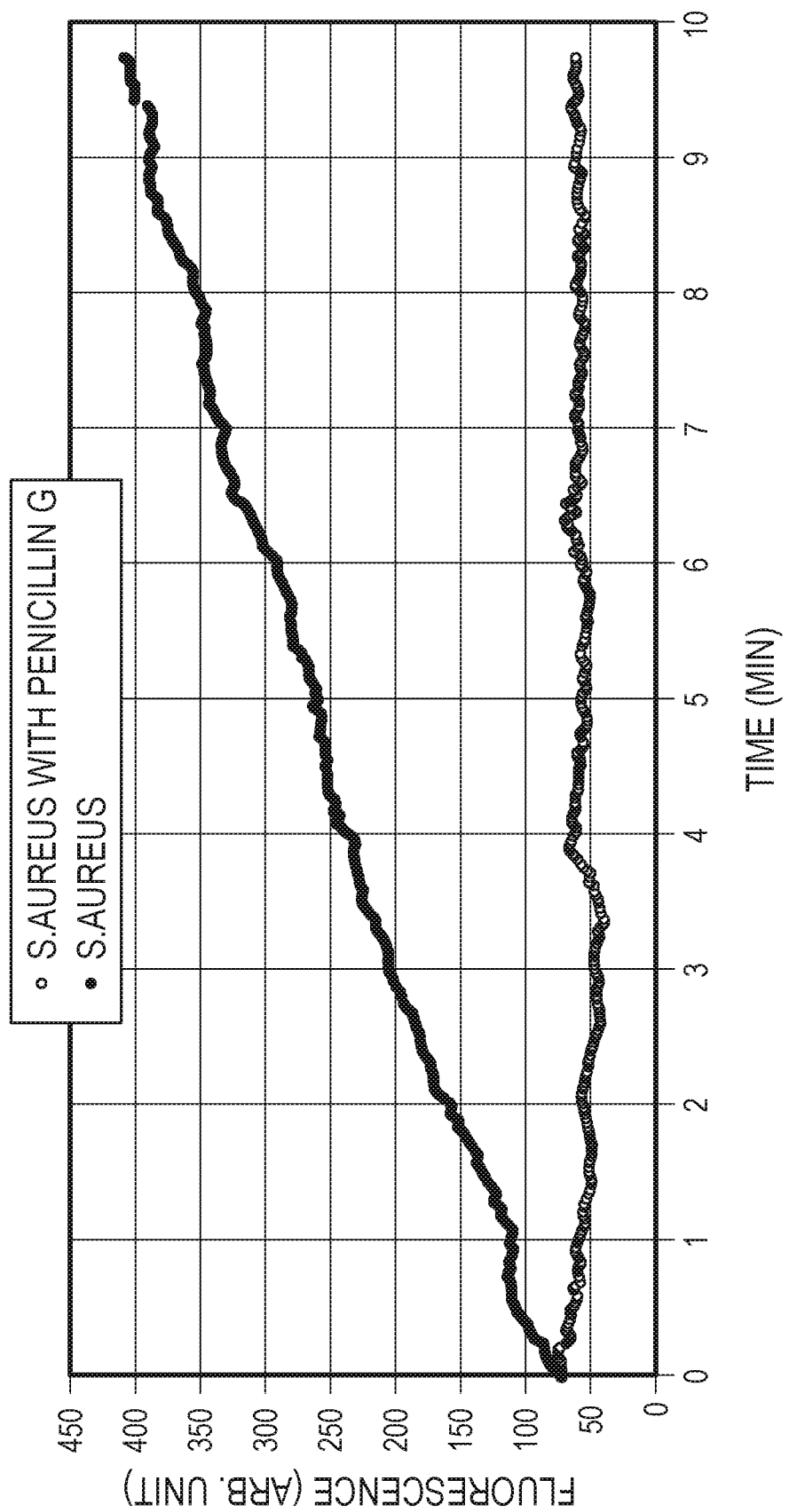
FIG. 8C is a graph that shows results of an experiment in which antibiotic susceptibility was determined using a detection reagent that is specific to a target analyte.

In another experiment, antibiotic susceptibility testing was performed for an antibiotic (e.g., Penicillin G) by comparing the fluorescence emitted by a sample that included a target pathogen (e.g., S. Aureus) and the fluorescence emitted by a control sample that did not include the antibiotic. FIG. 8C is a chart that shows results of the experiment. The experiment was performed using two liquid samples that were introduced into a microfluidic device and monitored for fluorescence over a 10-minute time period. The first sample was a 50 μl sample that included 2.5e6 colony forming units (CFU)/ml of S. Aureus, a fluorescent probe, and a Penicillin G solution as a test antibiotic. The second sample was a 50 μl sample that included 2.5e6 colony forming units (CFU)/ml of S. Aureus, a fluorescent probe, but did not include Penicillin G.

The results indicate that fluorescence intensity of the first sample (including Penicillin G) did not change significantly over the ten-minute time period, whereas fluorescence intensity of the second sample (without Penicillin G) did increase over the ten-minute time period. These results indicate that the S. Aureus bacteria preferentially cleaves penicillin G over the fluorescent probe, and therefore penicillin G is vulnerable to cleaving and should not be considered as a treatment option for S. Aureus or other β-lactamase producing bacteria.

OTHER IMPLEMENTATIONS

A number of implementations have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other implementations are within the scope of the following claims.

What is claimed is:

1. A portable system for detecting a change in fluorescence intensity in a liquid sample, the system comprising:
   a microfluidic device comprising:
      a housing comprising:
         an inlet that receives a liquid sample;
         an outlet for receiving the liquid sample from the inlet;
         a filter arranged between the inlet and the outlet and located to retain a target analyte; and
      a fluidic circuit arranged within the housing and comprising:
         a first channel in fluid communication with the inlet, wherein the first channel extends from the inlet to a first surface of the filter; and
         a second channel in fluid communication with the outlet, wherein the second channel extends from a second surface of the filter that is opposite to the first surface of the filter to the outlet, and is shaped and dimensioned to collect the liquid sample that has passed through the filter and has a depth that reduces an amount of unreacted detection reagent available to create background fluorescence during detection of the target analyte;
   an optical assembly comprising:
      an emission filter;
      a tube lens with a numerical aperture approximately equal to 0.4 and a focal length approximately equal to 3.3 millimeters; and
      an objective lens with a numerical aperture approximately equal to 0.79, a focal length approximately equal to 16 millimeters, and is coated with a 350 to 700 nanometer antireflective coating;
   an analyzer device configured to collect and process a fluorescent signal for the detection of the target analyte produced by a target pathogen, if present, in the liquid sample;
   one or more interface electronics; and
   a control circuit connected to an external interface of the analyzer device and configured to transmit control signals to the one or more interface electronics, wherein the analyzer device is configured to transmit signals to the control circuit through the external interface of the analyzer device.

2. The system of claim 1, wherein the microfluidic device; and is constructed from multiple layers.

3. The system of claim 2, wherein the multiple layers comprise:
   a first layer comprising a first hole corresponding to the inlet and a second hole corresponding to the outlet;
   a second layer arranged adjacent to the first layer and comprising a first hole aligned with the first hole of the first layer, and a second hole aligned with the second hole of the first layer;
   a third layer arranged adjacent to the second layer and comprising a portion of the first channel in communication with the first hole of the second layer, and a hole aligned with the second hole of the second layer; and
   a fourth layer arranged adjacent to the third layer and comprising another portion of the first channel in communication with the portion of the first channel in the third layer, a hole aligned with the hole of the third layer, and a portion that is arranged adjacent to the first surface of the filter;
   a fifth layer arranged adjacent to the fourth layer and comprising a hole aligned to the portion of the first channel in the fourth layer, a portion attached to the second surface of the filter, and a hole aligned with the hole of the fourth layer;
a sixth layer arranged adjacent to the fifth layer and comprising the second channel in communication with the hole of the fifth layer;
a seventh layer arranged adjacent to the sixth layer; and
an eighth layer arranged adjacent to the seventh layer.

4. The system of claim 3, wherein the first, third, sixth, and eighth layers comprise an acrylic material, and the second, fourth, fifth, and seventh layers comprise a double-sided adhesive.

5. The system of claim 1, further comprising a flow control device coupled to the housing and in communication with the first channel through the outlet, wherein the flow control device is configured and controlled to supply a negative pressure to the fluidic circuit to cause a volume of liquid sample to pass through the filter towards the outlet.

6. The system of claim 5, wherein the flow control device includes a plug member that is slidably disposed within a second outlet of the housing, and the second outlet is in fluid communication with the first and second channels.

7. The system of claim 6, wherein the flow control device is a syringe fluidly coupled to the second outlet.

8. The system of claim 1, wherein the filter comprises pores that are sized to be smaller than the target analyte.

9. The system of claim 1, wherein at least one or both of the first surface of the filter and one or more surfaces defining the first channel are partially or entirely coated with a fluorescent probe specific to an enzyme produced by a target pathogen.

10. The system of claim 1, wherein the analyzer device is a mobile phone, and the fluorescent signal is collected by a camera of the mobile phone.

11. The system of claim 10, further comprising:
a housing comprising:
the optical assembly;
a holder for securing the mobile phone and aligning the camera of the mobile phone with the optical assembly;
the microfluidic device; and
a sample holder for securing the microfluidic device and aligning a region of the microfluidic device that includes a first chamber with the optical assembly.

12. The system of claim 1, further comprising:
a heating device placed adjacent to the microfluidic device, wherein the heating device is configured to provide heat to the microfluidic device;
a light source configured to provide excitation light to the liquid sample; and
wherein the analyzer device is configured to run software that controls (i) an amount of heat provided by the heating device to the microfluidic device, and (ii) a magnitude of the excitation light provided by the light source to the microfluidic device.

13. The system of claim 12, wherein the light source comprises one or more light emitting diodes.

14. The system of claim 1, wherein the analyzer device is configured to determine, based on processing the fluorescent signal, a clinical indicator associated with the detection of the target analyte.

15. The system of claim 14, wherein the clinical indicator is a level of a bacterial enzyme determined based on an intensity of the fluorescent signal.

16. The system of claim 1, wherein:
the external interface comprises a headphone jack of the analyzer device;
the control circuit connected to the headphone jack of the analyzer device; and configured to transmit control signals to the one or more interface electronics; and
wherein the analyzer device is configured to transmit signals to the control circuit through the headphone jack of the analyzer device.

17. The system of claim 1, wherein the emission filter comprises a 500 nanometer long pass emission filter.

18. A portable system for detecting a change in fluorescence intensity in a liquid sample, the system comprising:
a microfluidic device for retaining a target analyte from the liquid sample, wherein the microfluidic device comprises a channel that is shaped and dimensioned to have a depth that reduces an amount of unreacted detection reagent available to create background fluorescence during detection of the target analyte;
an optical assembly comprising:
an emission filter;
a tube lens with a numerical aperture approximately equal to 0.4 and a focal length approximately equal to 3.3 millimeters; and
an objective lens with a numerical aperture approximately equal to 0.79, a focal length approximately equal to 16 millimeters, and is coated with a 350 to 700 nanometer antireflective coating;
an analyzer device configured to collect and process a fluorescent signal for the detection of the target analyte produced by a target pathogen, if present, in the liquid sample;
one or more interface electronics; and
a control circuit connected to an external interface of the analyzer device and configured to transmit control signals to the one or more interface electronics, wherein the analyzer device is configured to transmit signals to the control circuit through the external interface of the analyzer device.

19. The system of claim 18, wherein the analyzer device is a mobile phone, and the fluorescent signal is collected by a camera of the mobile phone.

* * * * *